US005487976A

United States Patent [19]
Soderlund et al.

[11] Patent Number: 5,487,976
[45] Date of Patent: Jan. 30, 1996

[54] DNA ENCODING AN INSECT GAMMA-AMINOBUTYRIC ACID (GABA) RECEPTOR SUBUNIT CELLS EXPRESSING IT, AND PESTICIDE SCREENING METHODS USING SUCH CELLS

[75] Inventors: David M. Soderlund; Douglas C. Knipple, both of Geneva; Joseph E. Henderson, Phelps, all of N.Y.

[73] Assignee: Cornell Research Foundation, Inc., Ithaca, N.Y.

[21] Appl. No.: 137,614

[22] Filed: Oct. 15, 1993

[51] Int. Cl.$^6$ .............................. C12N 15/12; C12N 5/00; C12N 1/11; G01N 33/68
[52] U.S. Cl. .................. 435/7.21; 435/69.1; 435/320.1; 435/240.2; 435/252.3; 435/254.11; 536/23.5
[58] Field of Search ...................... 536/23.5; 435/69.1, 435/320.1, 240.2, 7.1, 7.2, 7.21, 252.3, 254.4

[56] References Cited

U.S. PATENT DOCUMENTS 5,166,066  11/1992  Carter ...................................... 435/240.2

OTHER PUBLICATIONS ffrench–Constant, R., et al. (1993) J. Neurochem. 60: 2323–26.
ffrench–Constant et al. (1993) J. Neurochem. 60: 2323–26.
Pritchett, D. B., et al. (1989) Science 245:1389–92.
Thompson, M., et al. (1993) FEBS Lett. 325:187–90.
Barnard, E. A., et al., "Molecular Biology of the GABA$_A$ Receptor: the Receptor/Channel Superfamily" *Trends Neurosci* 10(12):502–509 (1987).
Burt, D. R., et al. "GABA$_A$ Receptor Subtypes: From Pharmacology to Molecular Biology" *The FASEB Journal* 5:2916–2923 (Nov. 1991).
Enna, S. J., et al., "GABA Receptors: An Overview", In: *Benzodiazepine/GABA Receptors and Chloride Channels:* *Structural and Functional Properties*, pp. 41–56, Alan R. Liss, Inc. (1986).
Langosch, D. et al., "Review–The Inhibitory Glycine Receptor: A Ligand–Gated Chloride Channel of the Central Nervous System", *Eur. J. Biochem.* 194:1–8 (1990).
Lummis, S. C. R. et al., "Transmembrane Signalling in Insects" *Annu. Rev. Entomol.* 35:345–377 (1990).
Sattelle, D. B., "GABA Receptors of Insects" *Advances in Insect Physiology* 22:1–113 (1990).
Schofield, P. R., "The GABA$_A$ Receptor: Molecular Biology Reveals a Complex Picture" *Trends Pharmacol Sci* 10:476–478 (1989).
ffrench–Constant, et al., 1991, *Proc. Natl. Acad. Sci. USA*, vol. 88, pp. 7209–7213. Copy obtained by Examiner–has been considered.
ffrench–Constant, et al., 1993, *Nature*, vol. 363, pp. 449–451, copy obtained by Ex.–considered.
Harvey, et al., 1991, *EMBO J.*, vol. 10, pp. 3239–3245, Copy obtained by Exr.–considered.
Henderson, et al., 1993, *Biochem. Biophys. Res. Commun.*, vol. 193(2), pp. 474–482.

*Primary Examiner*—Garnette D. Draper
*Assistant Examiner*—David L. Fitzgerald
*Attorney, Agent, or Firm*—Nixon, Hargrave, Devans & Doyle

[57] ABSTRACT

The present invention provides for the isolation of genomic DNA fragments from *Drosophila melanogaster* encoding conserved amino acid sequence elements unique to the ligand-gated chloride channel gene family. A polymerase chain reaction (PCR)-based homology probing strategy was utilized to isolate the genomic DNA fragments. Using the PCR strategy, three discrete amplified sequence elements designated LCCH1, LCCH2 and LCCH3, were isolated, LCCH2 and LCCH3 being novel. In another aspect of the present invention, there is provided the cloning and characterization of a cDNA encoding a novel member of the ligand-gated chloride channel gene family of insects isolated from *Drosophila melanogaster*. The cDNA corresponds to the LCCH3 genomic sequence of the invention.

8 Claims, 11 Drawing Sheets

FIG. 1B

| | |
|---|---|
| LCCH1 | ATPARVALGVTTTVLTMTTLMSSTNAALPKISYVKSIDVYLGTCFVMVFASLL——— |
| LCCH2 | ATADRVSLGITTTVLTMTFLGLEARTDLPKVSYPTALDFFVLSFGFIFATILQFAVV |
| LCCH3 | ATSARVALGITTTVLTMTTISTGVRSSLPRISYVKAIDIYLCMCFVFVFAALLEYAAV |
| Lym β | ATSARVALGITTTVLTMTTISNGVRSSLPRISYVKAIDIYLVMCFVFVFAALLEYAAV |
| α1 | SVPARTVFGVTTTVLTMTTLSISARNSLPKVAYATAMDWFIAVCYAFVFSALIEFATV |
| β1 | ASAARVALGITTTVLTMTTISTHLRETLPKIPYVKAIDIYLMGCFVFVFLALLEYAFV |
| γ2 | AVPARTSLGITTTVLTMTLSTIARKSLPKVSYVTAMDLFVSVCFIFVFSALVEYGTL |
| δ | AVPARVSLGITTTVLTMTTLMVSARSSLPKVSYVKAIDVYFWICYVFVFAALVEYAFA |
| Glα | AAPARVGLGITTTVLTMTTQSSGSRASLPKVSYVKAIDIWMAVCLLFVFSALLEYAAV |

FIG. 4A

```
  1  ATG ACA TGT TTT ACG CGC GTC GGA GTA TCC TGT AGC CTG TTC TTT TTC CTA CTG GGC GCC
-20  Met Thr Cys Phe Thr Arg Val Gly Val Ser Cys Ser Leu Phe Phe Phe Leu Leu Gly Ala

61  CAG CTA CAA TTG ATT CGA TGC ATT CGA AAG GAT GTA CTA GCT GGC CGC CTT GAG AAC GTC
  1  Gln Leu Gln Leu Ile Arg Cys Ile Arg Lys Asp Val Leu Ala Gly Arg Leu Glu Asn Val

121  ACG CAA ACA ATA TCA AAC ATA CTG CAA GGA TAC GAT ATT CGA CTT AGG CCC AAT TTC GGA
 21  Thr Gln Thr Ile Ser Asn Ile Leu Gln Gly Tyr Asp Ile Arg Leu Arg Pro Asn Phe Gly

181  GGA CCA CTA CAT GTC GGC ATG GAT TTG ACC ATC GCC AGC TTT GAT GCC ATA TCA GAA
 41  Gly Pro Leu His Val Gly Met Asp Leu Thr Ile Ala Ser Phe Asp Ala Ile Ser Glu

241  GTT AAC ATG GAT TAT ACG ATA ACA ATG TAT TTA AAT CAG TAT TGG CGC GAC GAG CGT TTG
 61  Val Asn Met Asp Tyr Thr Ile Thr Met Tyr Leu Asn Gln Tyr Trp Arg Asp Glu Arg Leu

301  GCA TTT AAT ATC TTT GGA CAA TAT TTC GAC GAT GGC AAT GAG GAT GGC ATA AGC GAT GTG
 81  Ala Phe Asn Ile Phe Gly Gln Tyr Phe Asp Asp Gly Asn Glu Asp Gly Ile Ser Asp Val

361  CTG ACA TTA TCC GGA GAC TTT GCT GAA AAG ATA TGG GTA CCG GAT ACG TTC TTC GCC AAT
101  Leu Thr Leu Ser Gly Asp Phe Ala Glu Lys Ile Trp Val Pro Asp Thr Phe Phe Ala Asn

421  GAC AAA AAC AGT TTT CTG CAC GAT GTC ACC GAA AGG AAC AAA CTG GTG CGA CTT GGC GGC
121  Asp Lys Asn Ser Phe Leu His Asp Val Thr Glu Arg Asn Lys Leu Val Arg Leu Gly Gly
```

FIG. 4B

```
481  GAT GGA GCT GTT ACT TAT GGC ATG AGA TTC ACC ACG GCC CTC TGC ATG ATG GAT CTG
141  Asp Gly Ala Val Thr Tyr Gly Met Arg Phe Thr Thr Leu Ala Cys Met Met Asp Leu
                                                              *

541  CAC TAC TAT CCA TTG GAC TCG CAG AAT TGC ACT GTG GAA ATT GAG AGC TAT GGA TAC ACG
161  His Tyr Tyr Pro Leu Asp Ser Gln Asn Cys Thr Val Glu Ile Glu Ser Tyr Gly Tyr Thr
                                     *

601  GTC AGC GAT GTG ATG TAC TGG AAG CCA ACG GTG CGC GGA GTG GAG GAT GCG GAG
181  Val Ser Asp Val Met Tyr Trp Lys Pro Thr Val Arg Gly Val Glu Asp Ala Glu

661  CTG CCG CAG TTC ACC ATC ATT GGG TAT GAG ACC AAT GAC CGA AAG GAG CGG CTG GCC ACT
201  Leu Pro Gln Phe Thr Ile Ile Gly Tyr Glu Thr Asn Asp Arg Lys Glu Arg Leu Ala Thr

721  GGA GTC TAT CAG CGC CTC TCG CTC TCA TTC AAA CTG CAA CGG AAT ATC GGA TAC TTT GTA
221  Gly Val Tyr Gln Arg Leu Ser Leu Ser Phe Lys Leu Gln Arg Asn Ile Gly Tyr Phe Val

781  TTC CAA ACT TAT CTG CCC AGC ATT CTG ATC GTA ATG CTG TCG TGG GTC TCG TTC TGG ATT
241  Phe Gln Thr Tyr Leu Pro Ser Ile Leu Ile Val Met Leu Ser Trp Val Ser Phe Trp Ile

841  AAC CAC GAG GCG ACG AGT GCC CGG GTT GCA TTG GGC ATC ACC ACG GTG CTC ACC ATG ACC
261  Asn His Glu Ala Thr Ser Ala Arg Val Ala Leu Gly Ile Thr Thr Val Leu Thr Met Thr

901  ACC ATT AGC AGC ACG GGT GTT CGC AGC TCA CTG CCG CGC ATA TCG TAT GTG AAG GCG ATC GAC
281  Thr Ile Ser Ser Thr Gly Val Arg Ser Ser Leu Pro Arg Ile Ser Tyr Val Lys Ala Ile Asp
```

```
961   ATT TAT CTG GTC ATG TGC TTC GTG TTC GCA GCC CTC TTG GAA TAC GCT GCC GTT
301   Ile Tyr Leu Val Met Cys Phe Val Phe Ala Ala Leu Leu Glu Tyr Ala Ala Val

1021  AAC TAT ACT TAC TGG GGC AAA AGG GCT AAA ATA AAG AAA GTC AAA GAA TGT TGT
321   Asn Tyr Thr Tyr Trp Gly Lys Arg Ala Lys Ile Lys Lys Val Lys Glu Cys Cys

1081  CCA GGC AAG ATC GGA AAG AGT GAA AGA TCC GAG ACG TGT TCA ACG GAG GAC ATT ATC
341   Pro Gly Lys Ile Gly Lys Ser Glu Arg Ser Glu Thr Cys Ser Thr Glu Asp Ile Ile

1141  GAG CTG CAG GAT GTT CGA AGT ATG CCT ATA CCA TCT TTG CGA AGA GGT ACC TAC AAT GCC
361   Glu Leu Gln Asp Val Arg Ser Met Pro Ile Pro Ser Leu Arg Arg Gly Thr Tyr Asn Ala

1201  ACC CTC GAC TCC ATC GGC ACC GAG AAT CTA GGA AAG TTC CCC CCA AGG GGT ATC
381   Thr Leu Asp Ser Ile Gly Thr Glu Asn Leu Gly Lys Phe Pro Pro Arg Gly Ile

1261  ATA ACT CGT AAT TAT GGC ACC CGC ATG TTG CAC GCC CTG AAG AGA CGT CGC CAA AGG GGT ATC
401   Ile Thr Arg Asn Tyr Gly Thr Arg Met Leu His Ala Leu Lys Arg Arg Arg Gln Arg Gly Ile

1321  TCA ACC CGC CCA ATC AAA GAT GTC AAT ATT ATT GAC AAA TAC TCC CGA ATG ATA TTT CCG ATC
421   Ser Thr Arg Pro Ile Lys Asp Val Asn Ile Ile Asp Lys Tyr Ser Arg Met Ile Phe Pro Ile

1381  ATA CCG AAG ATC CTT GAC AAG ATC CTT TAT ATT CTG GAA
441   Ile Pro Lys Ile Leu Asp Lys Ile Leu Tyr Ile Leu Glu

1441  AGT TTT CTT GCG TTC AAT CTT GGC TAC TGG CTG TTT TAT ATT CTG GAA tga
461   Ser Phe Leu Ala Phe Asn Leu Gly Tyr Trp Leu Phe Tyr Ile Leu Glu ***
```

```
Dm LCCH3      .....MTCF TRVGVSC.SL FFFLLGAQLQ L..........  IRCIRKDVLA    14
Lymnaea β     .........  MWGIIVP.FF SASIMCSLVA V..........  VRCQQD...T     4
Rat β1        .........  MWTVQNRESL GLLSFPVMVA M..........  VCCAHSSNEP     6
Dm Rdl        MSDSKMDKLA RMAPLPRTPL LTIWLAINMA LIAQETGHKR   IHTVQAATGG    17

Dm LCCH3      GRL...ENVT QTISNILQCY DIRIRPNFGG  EPLHVGMDLT  IASFDAISEV    61
Lymnaea β     DHF...ANVT NTIDSLLKGY DIRLRPSFGG  APLEIGIEVI  LASFDSISEV    51
Rat β1        SNM...SYVK ETVDRLLKGY DIRLRPDFGG  PPVDVGMRID  VASIDMVSEV    53
Dm Rdl        GSMLGDVNIS AILDSFSVSY DKRVRPNYGG  PPVEVGVTMY  VISISSVSEV    67

Dm LCCH3      NMDYITMYL  NQYWRDERIA FNIFGQYFDD  ENDDGISDVL  TLSGDFAEKI   111
Lymnaea β     DMDYITMYL  NQYWRDERIQ F.IFNESLDL  GENRSVT.TM  TLTGAFAEKI   101
Rat β1        NMDYTLTMYF QQSWKDKRLS Y..........  ...SGIPLNL  TLDNRVADQL    91
Dm Rdl        LMDFTLDFYF RQFWIDPRIA Y..........  .RKRPGVETL  SVGSEFIKNI   107

Dm LCCH3      WVPDTFFAND KNSFLHDVIE RNKLVRLGGD  GAVTYGMRFT  TTLACMMDIH   161
Lymnaea β     WVPDTFLAND KNSFLHDITE KNKMVRLYGN  GSLVYGMRFT  TTLACMMDLH   151
Rat β1        WVPDTYFLND KKSFVHGVTV KNRMIRLHPD  GTVLYGLRIT  TTAACMMDLR   141
Dm Rdl        WVPDTFFVNE KQSYFHIATT SNEFIRVHHS  GSITRSIRIT  ITASCPMNLQ   157
```

FIG. 6B

```
Dm LCCH3     YYPLDSQNCT  VEIESYGYTV  SDVMYW..K   PTPVRGVEDA  ELPQFTIIGY  209
Lymnaea β    NYPLDHQECT  VEIESYGYTM  DDIVLYWLND  RGAVTGVEDV  SLPQFSITNY  201
Rat β1       RYPLDEQNCT  LEIESYGYTT  DDIEFYWNGG  EGAVTGVNKI  ELPQFSIVDY  191
Dm Rdl       YFPMDRQLCH  IEIESFGYTM  RDIRYFWRDG  LSSVGMSSEV  ELPQFRVLGH  207

Dm LCCH3     ETNDRKERLA  TGVYQRISLS  FKLQRNIGYF  VFQTYLPSIL  IVMLSWVSFW  259
Lymnaea β    ATINKIEELS  TGDYQRLSLI  FQLQRNIGYF  IFQTYLPSIL  IVMLSWVSFW  251
Rat β1       KMVSKKVEFT  TGAYPRLSLS  FRLKRNIGYF  ILQTYMPSTL  ITILSWVSFW  241
Dm Rdl       RQRATEINLI  TGNYSRLACE  IQFVRSMGYY  LIQIYIPSGL  IVVISWVSFW  257

Dm LCCH3     INHEATSARV  ALGITTVLTM  TTISTGVRSS  LPRISYVKAI  DIYLVMCFVF  309
Lymnaea β    INHEATSARV  ALGITTVLTM  TTISNGVRSS  LPRISYVKAI  DIYLVMCFVF  301
Rat β1       INYDASAARV  ALGITTVLTM  TTISTHLRET  LPKIPYVKAI  DIYLMGCFVF  291
Dm Rdl       LNRNATPARV  ALGVTTVLTM  TTLMSSTNAA  LPKISYVKSI  DVYLGTCFVM  307

Dm LCCH3     VFAALLEYAA  VNYTYWGKRA  KKKIKKVKEC  CPGKIGKSE.  ....RSETCST  355
Lymnaea β    VFAALLEYAA  VNYTYWGARA  KRKAKRLRER  ATSVRKRVD.  ....DGDQMNN  347
Rat β1       VFLALLEYAF  VNYIFFGKGP  QKKGASKQDQ  SANEKNKLEM  NKVQVDAHGN  341
Dm Rdl       VFASLLEYAT  VGYMAKRIQM  RKQRFMAIQK  IAEQKKQQLD  GANQQQANPN  357
```

```
Dm LCCH3    TE.DIIELQD VRMSP..IPS LRRGTY..... .......... ..........  378
Lymnaea β   TNMDTVELKE VHMVPTSVGV TNSQSF..... .......... ..........  373
Rat β1      ILLSTLEIRN ETSGSEVLTG VSDP...... .......... ..........  365
Dm Rdl      PNANVGGPGG VGVGPGGPGG PGGGVNVGVG MGMGPEHGHG HGHHAHSHGH  407

Dm LCCH3    .NATLDSIGT ETMNLGKFP. .......... .......... ..........  396
Lymnaea β   .NLDLDDGSG DDTGFRVVP. .......... .......... ..........  391
Rat β1      .KATMYSYDS ASIQYRKPL. .......... .......... ..........  383
Dm Rdl      PHAPKQTVSN RPIGFSNIQQ NVGTRGCSIV GPLFQEVRFK VHDPKAHSKG  457

Dm LCCH3    .......... ...PSFR.IT RNYGTGHSQL ......RRRA QRGISTRPRM  426
Lymnaea β   .......... ...PIPRSFT HSHATTHGYI PTNVRRRSS. SHVPPRRRRL  428
Rat β1      .......... ...SSREGFG RGLD...... .......... RHGVPGKGR.  403
Dm Rdl      GTLENTVNGG RGGPQSHGPG PGQGGGPPGG GGGGGGGGGP PEGGDPEAA  507

Dm LCCH3    LHALKRGASA IKATIPKIKD V..NIIDKYS RMIFPISFLA FNLGYWLFYI  474
Lymnaea β   LSHFRQKAKS IKVKIPRVQD V..NTIDKYA RLMFPLLFII FNTSYWSVYL  476
Rat β1      ...IRRRASQ LKVKIPDLTD V..NSIDKWS RMFFPITFSL FNVVYWLYYV  448
Dm Rdl      VPAHLLHPGK VKKDINKLLG ITPSDIDKYS RIVFPVCFVC FNLMYWIIYL  557

Dm LCCH3    LE*....... .......... .......... .......... ..........  476
Lymnaea β   LT*....... .......... .......... .......... ..........  478
Rat β1      H*........ .......... .......... .......... ..........  449
Dm Rdl      HVSDVVADDL VLLGEE*     573
```

FIG. 6C

DNA ENCODING AN INSECT GAMMA-AMINOBUTYRIC ACID (GABA) RECEPTOR SUBUNIT CELLS EXPRESSING IT, AND PESTICIDE SCREENING METHODS USING SUCH CELLS

This invention was made in part with government support under Grant Number ES070520 awarded by the National Institute of Environmental Health Sciences, and the government has certain rights herein.

FIELD OF THE INVENTION

The present invention relates generally to the ligand-gated chloride channel gene family. More particularly, the present invention relates to the characterization and isolation of an insect γ-aminobutyric acid (GABA) receptor subunit gene from *Drosophila melanogaster*.

BACKGROUND OF THE INVENTION

γ-Aminobutyric acid (GABA) is the principal inhibitory neurotransmitter in the vertebrate brain, in the insect central nervous system and at insect neuromuscular junctions (Enna et al., 1986, In Benzodiazepine/GABA Receptors and Chloride Channels: Structural and Functional Properties, Alan R. Liss, Inc., New York, pp. 41–56; and Sattelle, D. B., 1990, *Adv. Insect Physiol.*, vol. 22, pp. 1–113). Mammalian genes encoding at least 5 distinct classes of GABA receptor subunits, i.e., α, β, γ, δ, and ρ, have been cloned and characterized (Burr et al., GABA$_A$ receptor subtypes: from pharmacology to molecular biology, 1991, *FASEB/J.*, vol. 5, 2916–2923). Genes encoding vertebrate GABA receptor subunits and the strychnine-binding subunit of the glycine-gated chloride channel comprise a family of homologous ligand-gated chloride channel genes, which is part of a larger superfamily of ligand-gated ion channel genes (Barnard et al., 1987, *Trends Neurosci.*, vol. 10, pp. 502–509). Gene products of this superfamily have a conserved structural organization with four hydrophobic membrane-spanning domains. GABA stimulates chloride ion conductance through the associated chloride ion channel. The predominant effect of GABA is the interaction with a specific receptor protein which results in an increase of chloride ion conductance to produce an inhibition of neuronal firing. Heterologous expression in vitro of different combinations of GABA receptor subunit types (α, β, γ, δ, etc.) and subunit isoforms (α1, α2, etc.) results in heteromultimeric receptors with differing structure and pharmacology (Schofield, P. R., The GABA$_A$ receptor: molecular biology reveals a complex picture, 1989, *Trends Pharmacol. Sci.*, vol. 10, pp. 476–478; and Burt et al., GABA$_A$ receptor subtypes; from pharmacology to molecular biology, 1991, *FASEB/J.*, vol. 5, 2916–2923). It is thought that the differential expression of subunits in different cell types is the molecular basis of the known pharmacological diversity of GABA receptors in the mammalian central nervous system (Burt et al., 1991, cited elsewhere herein).

Electrophysiological studies of ligand-gated ion currents in insect nerve and muscle cells provide evidence for the existence of chloride channels gated by glutamate, histamine, and taurine, as well as those gated by GABA (Sattelle, D. B., 1990, cited elsewhere herein; and Lummis et al., 1990, *Annu. Rev. Entomol.*, vol. 35, pp. 345–377). Although these findings imply the existence of a large and diverse gene family encoding ligand-gated chloride channels in insects, very little is known of about homologous channels of invertebrates. Only a single gene from insects having a significant degree of structural conservation and amino acid sequence identity with vertebrate ligand-gated chloride channel genes has been described (ffrench-Constant et al., 1991, *Proc. Natl. Acad. Sci. USA*, vol. 88, pp. 7209–7213). Here, a *Drosophila melanogaster* cDNA having significant predicted amino acid sequence identity to vertebrate ligand-gated chloride channel genes was isolated and mapped to a genetic locus (Rdl) that confers resistance to cyclodiene insecticides and other blockers of GABA-gated chloride channels. Rdl was shown to encode a GABA receptor subunit by the expression of functional homomultimeric GABA receptors in Xenopus oocytes following injection with Rdl mRNA (ffrench-Constant et al., 1993, *Nature*, vol. 363, pp. 449–451).

The only other example of a ligand-gated chloride channel gene from an invertebrate species is a GABA receptor β-like subunit gene isolated from the pond snail, *Lymnaea stagnalis* (Harvey et al., 1991, *EMBO/J.*, vol. 10, pp. 3239–3245). The functional relationship of the product encoded by this gene to vertebrate GABA receptor β subunits was corroborated by the formation of a functional chimeric receptor with properties similar to vertebrate α/β heteromultimers when the gene was co-expressed with a vertebrate α subunit in Xenopus oocytes.

The γ-aminobutyric acid (GABA) receptor-chloride channel complex mediates synaptic inhibition in both vertebrate and invertebrate nervous systems and is a target site for a variety of drugs, toxicants, and insecticides (Enna et al., 1986 and Sattelle, 1990, cited elsewhere herein). That is, GABA receptors of insects are known to be target sites for chemical agents having insecticidal or pesticidal activity. Furthermore, invertebrate GABA receptors have different pharmacological properties as compared to those of vertebrate GABA receptors. Therefore, the characterization and isolation of an invertebrate GABA receptor subunit gene(s) would be useful in developing screening techniques to identify insect-specific pesticides.

SUMMARY OF THE INVENTION

The primary object of the present invention is the isolation and characterization of an invertebrate (i.e., insect) γ-aminobutyric acid (GABA) receptor subunit gene(s).

The present invention provides for the isolation of genomic DNA fragments from *Drosophila melanogaster* which encode for conserved amino acid sequence elements unique to the ligand-gated chloride channel gene family. A polymerase chain reaction (PCR)-based homology probing strategy was utilized to isolate the genomic DNA fragments of the invention. As described herein, these DNA fragments are designated "LCCHs", which refers to ligand-gated chloride channel gene homologues.

Using the PCR strategy, three discrete amplified sequence elements designated LCCH1, LCCH2 and LCCH3, were isolated. LCCH1, LCCH2 and LCCH3 contained open reading frames and >40% amino acid sequence identity to the corresponding regions of vertebrate ligand-gated chloride channel genes. Genomic DNA clones corresponding to each sequence element were isolated and sequenced, and predicted amino acid sequences corresponding to the second (M2) and third (M3) transmembrane domains of vertebrate genes were analyzed for identity or similarity to known sequences.

In another aspect of the present invention, there is provided the cloning and characterization of a cDNA encoding a novel member of the ligand-gated chloride channel gene family of insects isolated from *Drosophila melanogaster*, the LCCH3 genomic sequence of the invention. The 1488 nucleotide open reading frame of this cDNA encodes an amino acid sequence having structural features conserved among ligand-gated chloride channel subunit proteins, including four hydrophobic domains capable of forming transmembrane helices (M1–M4), an octapeptide "signature motif" occurring in M2, a large intracellular domain between M3 and M4, and cysteine residues postulated to form a disulfide-bridged loop structure in the extracellular domain. The LCCH3 gene of the present invention exhibited the greatest similarity to GABA receptor β subunit genes. This high level of structural similarity suggests that its encoded protein may be a functional homologue of the β subunit family in the *Drosophila melanogaster* nervous system.

The DNA sequences and corresponding amino acid sequences encoding the γ-aminobutyric acid (GABA) receptor subunit gene(s) of the invention may be cloned into any suitable expression vector, such as, for example, plasmid DNA, viral DNA including human viruses, animal viruses and insect viruses and bacteriophages to form a recombinant expression system which directs the expression of the subunits of the invention.

The expression system, which directs the expression of the GABA receptor subunit(s) of the invention, in combination with at least one other vertebrate and/or invertebrate GABA receptor subunit gene, can be co-expressed in an appropriate host cell to form a functional recombinant GABA receptor.

A method of screening chemical agents for their effectiveness as pesticides using the γ-aminobutyric acid (GABA) receptor subunit gene(s) of the invention is also disclosed.

BRIEF DESCRIPTION OF THE DRAWINGS

FIG. 4 illustrates the nucleotide and inferred amino acid sequences of LCCH3.

FIG. 6 illustrates the alignment of the predicted amino acid sequence of the present isolated gene fragment (LCCH3) with those of the *Lymnaea stagnalis* GABA receptor β-like subunit ("Lymnaea β"), the rat GABA receptor β1 subunit ("rat β1"), and the *Drosophila melanogaster* Rdl locus ("Dm Rdl") using the GCG computer program.

DETAILED DESCRIPTION OF THE INVENTION

The present invention provides for the isolation of genomic DNA fragments from *Drosophila melanogaster*. These fragments encode for conserved amino acid sequence elements unique to the ligand-gated chloride channel gene family. A polymerase chain reaction (PCR)-based homology probing strategy was utilized to isolate these genomic DNA fragments. Use of this PCR strategy yielded three DNA fragment sequence elements designated LCCH1, LCCH2 and LCCH3, from *Drosophila melanogaster*. These sequence elements appear to represent structurally divergent members of the ligand-gated chloride channel gene family. Two of these sequence elements, LCCH2 and LCCH3, are novel sequences.

It is understood that the sequence elements designated LCCH1, LCCH2 and LCCH3 are for purposes of illustration only, and the existence of a diverse family of genes in *Drosophila melanogaster* that are structurally related to the ligand-gated chloride channel gene family of vertebrates is supported by the present invention.

In another aspect of the present invention, there is provided the cloning and characterization of a cDNA encoding a novel member of the ligand-gated chloride channel gene family of insects isolated from *Drosophila melanogaster*. The cDNA corresponds to the LCCH3 genomic sequence of the invention. In this context, the novel sequence elements LCCH2 and LCCH3 of the invention exhibit all the conserved features commonly found in members of the family of ligand-gated chloride channel genes. More specifically, the sequence elements of the present invention exhibit: (1) a structural organization encompassing a large N-terminal extracellular domain, (2) four hydrophobic domains (M1, M2, M3, and M4) capable of forming transmembrane helices, as well as a large intracellular domain lying between transmembrane domains M3 and M4, (3) the conserved octapeptide -TTVLTMTT- (SEQ.ID.NO.1) "signature motif" for this gene family found in transmembrane domain M2, and (4) the conserved cysteine residues and associated sequence elements capable of forming a disulfide-bridged loop structure in the large extracellular domain.

In one embodiment of the present invention, there is provided an isolated gene and/or gene fragment or portion thereof comprising a DNA molecule encoding an γ-aminobutyric acid (GABA) receptor subunit from *Drosophila melanogaster*. Preferably, the DNA molecule of the invention encodes for an amino acid sequence, or mutant thereof, corresponding to LCCH3, as shown in FIG. 4, SEQ. ID. NO. 2. The DNA molecule of the present invention preferably comprises a nucleotide sequence, or a mutant DNA sequence thereof, corresponding to LCCH3, as shown in FIG. 4, SEQ. ID. NO. 3.

Figure 1A:
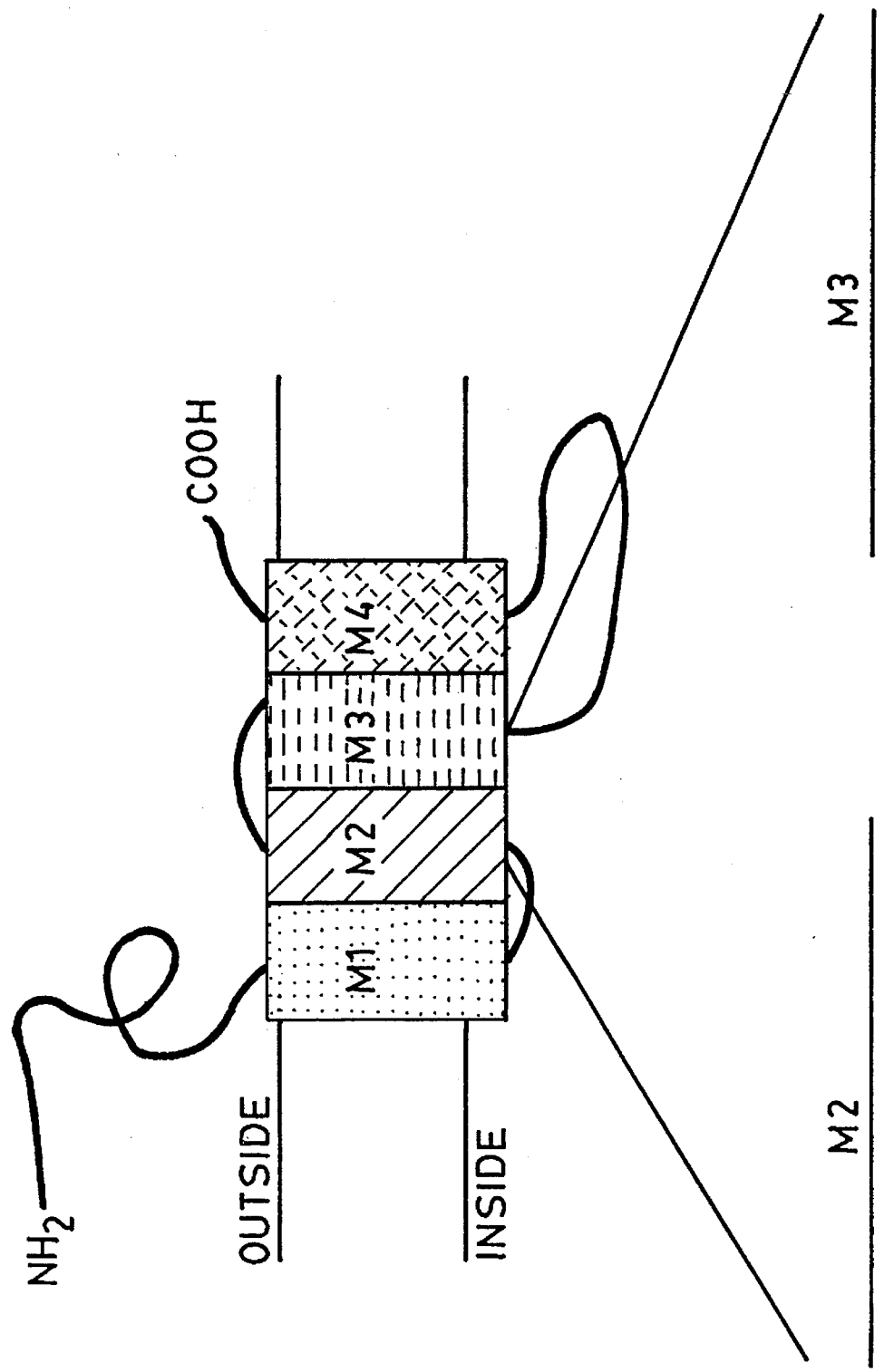
FIG. 1 is a schematic diagram of a single ligand-gated chloride channel subunit depicting the inferred transmembrane (M1–M4) and hydrophobic domains, and the expanded M2–M3 region.

In still another embodiment of the invention, the DNA molecule encodes for an amino acid sequence, or mutant thereof, corresponding to LCCH2, as shown in FIG. 1, SEQ. ID. NO. 16.

It is understood that any modifications i.e., insertions, deletions, mutations, recombinants, etc., of the DNA nucleotide and/or corresponding amino acid sequence(s) are within the scope of the present invention provided that the modified sequence(s) encode for a gene, its homologs or a fragment thereof producing an γ-aminobutyric acid (GABA) receptor subunit from *Drosophila melanogaster*. Preferably, this receptor subunit exhibits pharmacological properties of γ-aminobutyric acid receptors in insect tissue.

Recombinant DNA techniques are used to insert the DNA sequences of the invention (e.g. GABA receptor subunit from *Drosophila melanogaster*) into an appropriate expression vector, i.e., a vector which contains the necessary elements for the transcription and translation of the inserted coding sequences. A large number of vector systems known in the art can be used, such as, plasmids, bacteriophage virus or other modified viruses. Suitable vectors include, but are not limited to the following viral vectors such as lambda vector system gt11, gtWES.tB, Charon 4, and plasmid vectors such as pBR322, pBR325, pACYC177, pACYC184, pAR series, pKK223-3, pUC8, pUC9, pUC18, pUC19, pLG339, pR290, pKC37, pKC101 and other similar systems. The DNA sequences are cloned into the vector using standard cloning procedures in the art, as described by Maniatis et al., 1982, *Molecular Cloning: A Laboratory Manual*, Cold Spring Harbor Laboratory, Cold Springs Harbor, N.Y., which disclosure is hereby incorporated by reference.

The recombinant DNA molecule (e.g., vector+ sequence of invention) can then be introduced into appropriate host cells, including but not limited to bacteria, virus, yeast, mammalian cells or the like. The vector system must be compatible with the host cell used. The recombinant vectors can be introduced into the host cells via transformation, transfection or infection using standard techniques in the art. A variety of host cell systems can be used to express the GABA receptor subunit gene of the invention. For example, host cell systems include, but are not limited to the following: bacteria transformed with bacteriophage DNA, plasmid DNA or cosmid DNA such as *E. coli* JM103, *E. coli* C600, *E. coli* CO4, *E. coli* DH20 and *E. coli* TB1; microorganisms such as yeast containing yeast vectors; mammalian cell systems infected with virus (vaccinia virus, adenovirus, etc.); insect cell systems infected with virus (baculovirus).

In order to obtain efficient expression of the GABA receptor subunit gene, a promotor must be present in the expression vector. RNA polymerase normally binds to the promotor and initiates transcription of a gene or a group of linked genes and regulatory elements (operon). Promoters vary in their strength, i.e., ability to promote transcription. For the purpose of expressing the gene of the invention, it is desirable to use strong promoters in order to obtain a high level of transcription and, hence, expression of the gene. Depending upon the host cell system utilized, any one of a number of suitable promoters can be used, such as, the lac promotor, trp promotor, recA promotor, ribosomal RNA promotor, the $P_R$ and $P_L$ promoters of coliphage lambda and others including but not limited to lacUV5, ompF, bla, lpp and the like, nos promoter, the small subunit ribulose bisphosphate carboxylase genes, the small subunit chlorophyll A/B binding polypeptide, the 35S promoter of cauliflower mosaic virus, and promoters isolated from plant genes, including the Pto promoter itself (Vallejos, et al., 1986, *Genetics*, vol. 112, pp. 93–105, which disclosure is hereby incorporated by reference) to direct high levels of transcription of adjacent DNA segments. Additionally, a hybrid trp-lacUV5 (tac) promoter or other *E. coli* promoters produced by recombinant DNA or other synthetic DNA techniques can be used to provide for transcription of the gene of the invention.

Bacterial host cell strains and expression vectors can be chosen which inhibit the action of the promotor unless specifically induced. In certain operons the addition of specific inducers is necessary for efficient transcription of the inserted DNA; for example, the lac operon is induced by the addition of lactose or IPTG (isopropylthio-beta-D-galactoside). A variety of other operons, such as trp, pro, etc., are under different controls. The trp operon is induced when tryptophan is absent in the growth media; and the $P_L$ promotor of lambda can be induced by an increase in temperature in host cells containing a temperature sensitive lambda repressor, e.g., c1857. In this way, greater than 95% of the promotor-directed transcription may be inhibited in uninduced cells. Thus, expression of the gene of the invention can be controlled.

One such promotor/operator system is the so-called "tac" or trp-lac promotor/operator system (Russell and Bennett, 1982, *Gene*, vol. 20, pp.231–243, which disclosure is hereby incorporated by reference). This hybrid promoter is constructed by combining the −35 b.p. (−35 region) of the trp promotor and the −10 b.p. (−10 region or Pribnow box) of the lac promoter (the sequences of DNA which are the RNA polymerase binding site). In addition to maintaining the strong promotor characteristics of the tryptophan promotor, tac is also controlled by the lac repressor.

When cloning in a eucaryotic host cell, enhancer sequences (e.g., the 72 bp tandem repeat of SV40 DNA or the retroviral long terminal repeats of LTRs, etc.) may be inserted to increase transcriptional efficiency. Enhancer sequences are a set of eucaryotic DNA elements that appear to increase transcriptional efficiency in a manner relatively independent of their position and orientation with respect to a nearby gene. Unlike the classic promotor elements (e.g., the polymerase binding site and the Goldberg-Hogness "TATA" box) which must be located immediately 5' to the gene, enhancer sequences have the remarkable ability to function upstream from, within, or downstream from eucaryotic genes. Therefore, the position of the enhancer sequence with respect to the inserted gene is less critical.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires a Shine-Dalgarno (SD) sequence about 7–9 basis 5' to the initiation codon (ATG) to provide a ribosome binding site. Thus, any SD-ATG combination that can be utilized by host cell ribosomes can be employed. Such combinations include but are not limited to the SD-ATG combination from the CRO gene or the N gene of coliphage lambda, or from the *E. coli* tryptophan E, D, C, B or A genes. Additionally, any SD-ATG combination produced by recombinant DNA or other techniques involving incorporation of synthetic nucleotides can be used.

Any of the conventional cloning methods for insertion of DNA fragments into a vector can be used to ligate the promotor and other control elements into specific sites within the vector. Accordingly, gene sequences containing those regions coding for the GABA receptor subunit of the invention can be ligated into an expression vector at a specific site in relation to the vector promotor and control elements so that when the recombinant DNA molecule is introduced into a host cell the foreign genetic sequence can be expressed (i.e., transcribed and translated) by the host cell.

As previously mentioned, the recombinant DNA molecule can be introduced into appropriate host cells (including but not limited to bacteria, virus, yeast, mammalian cells or the like) by transformation, infection or transfection (depending upon the vector/host cell system). Transformants are selected based upon the expression of one or more appropriate gene markers normally present in the vector, such as ampicillin resistance or tetracycline resistance in pBR322, or thymidine kinase activity in eucaryotic host systems.

Expression of such marker genes should indicate that the recombinant DNA molecule is intact and is replicating. Expression vectors may be derived from cloning vectors, which usually contain a marker function. Such cloning vectors may include, but are not limited to the following: SV40 and adenovirus, vaccinia virus vectors, insect viruses such as baculoviruses, yeast vectors, bacteriophage vectors such as lambda gt-WES-lambda BC, lambda gt-1-lambda B, M13mp7, M13mp8, M13mp9, or plasmid DNA vectors such as pBR322, pAC105, pVA51, pACYC177, pKH47, pACYC184, pUB110, pMB9, pBR325, Col E1, pSC101, pBR313, pML21, RSF2124, pCR1, RP4, pBR328 and the like.

The expression vectors containing the foreign gene inserts (e.g., DNA encoding the GABA receptor subunit of the invention) can be identified by three approaches: (1) DNA-DNA hybridization using probes comprising sequences that are homologous to the gene(s); (2) presence or absence of "marker" gene function and (3) expression of inserted sequences based on physical, immunological or functional properties. Once a recombinant which expresses the gene is identified, the gene product should be analyzed. Immunological analysis is especially important because the ultimate goal is to use the gene or recombinant expression systems that express the gene in assays for screening chemical agents. Once the GABA receptor subunit is identified, it is cultured under conditions which facilitate growth of the cells and expression of the gene as will be apparent to one skilled in the art, then isolated and purified by standard methods including chromatography (e.g., ion exchange, affinity, and sizing column chromatography), centrifugation, differential solubility, or by any other standard techniques. In addition, since the amino acid sequence is known from the DNA sequence of the invention, the GABA receptor subunit can be synthesized by chemical methods according to the procedure of Hunkapiller et al., 1984, Nature, vol. 310, pp. 105–111, which disclosure is hereby incorporated by reference.

In order to obtain efficient expression of a functional GABA receptor, the gene, or fragment thereof, of the present invention is co-expressed with at least one other vertebrate or invertebrate GABA receptor subunit gene. This other GABA receptor subunit gene preferably is any α (alpha) or α (alpha) subunit-like sequence(s), such as, for example, the rat GABA receptor α1 subunit, the Drosophila melanogaster Rdl locus or gamma subunit sequence(s).

The functional GABA receptor produced by co-expression of the GABA receptor subunit gene of the present invention with at least one other vertebrate or invertebrate GABA receptor subunit, can be used to screen for pesticides that are effective in the control of insects such as Drosophila melanogaster. It is known that the insect GABA receptor forms a particularly attractive site for insecticides due to pronounced differences in its pharmacology with that of vertebrates, as described in ffrench-Constant et al., 1991, cited elsewhere herein, which disclosure is hereby incorporated by reference. Due to those differences in insect and vertebrate GABA receptor pharmacology, cells transformed to include the insect GABA receptor formed in accordance with the present invention can be exposed to various potential insecticides and pesticides and evaluated for their susceptibility to the agents to develop and identify insect control agents that will not cause adverse effects to vertebrate species. Exemplary methods of screening are described in Eldefrawei et al., 1987, FASEB/J., vol. 1, pp. 262–271; and Rauh et al., 1990, Trends in Pharmacol. Sci., vol. 11, pp. 325–329, which disclosures are hereby incorporated by reference.

The present invention is further illustrated by the following examples.

EXAMPLE I

METHODS

1. DNA Amplification:

Two homology probing procedures based on the use of PCR with degenerate oligonucleotide primers were employed. The first, a "single site" procedure (Roux et al., 1990, Biotechniques, vol. 8, pp. 48–57; and Knipple et al., 1991, Mol. Gen. Genet., vol. 226, pp. 241–249, which disclosures are hereby incorporated by reference), employed three 512-fold degenerate target primer pools (TP1a, TP1b, and TP1c; Table Table 1).

TABLE 1

| Name | Nucleotide sequence[2] | Strand[3] |
|---|---|---|
| Tailed linker[1] | 5'-GATCCTGTGAT-3' (SEQ. ID. No. 4) | |
| Anchor template[1] | 5'-AAGTCACGTCATGAGTCCGACAG-3' (SEQ. ID. No. 5) | |
| Anchor primer(AP)[1] | 5'-AAGTCACGTCATGAGTCC-3' (SEQ. ID. No. 6) | |
| Target Primer(TP1a) | 5'-GTAAAAGGACGGCCAGTCTAGAACNACNGTN(TC)TGACNATGAC-3' (SEQ. ID. No. 7) | + |
| Target Primer(TP1b) | 5'-GTAAAAGGACGGCCAGTCTAGAACNACNGTNCT(CT)ACNATGAC-3' (SEQ. ID. No. 8) | + |
| Target Primer(TP1c) | 5'-GTAAAAGGACGGCCAGTCTAGAACNACNGTN(CT)TAACNATGAC-3' (SEQ. ID. No. 9) | + |
| Target Primer(TP2) | 5'-GGGAATTC(AG)AANAC(AG)AANAC(AG)AA(AG)CA-3' (SEQ. ID. No. 10) | − |

[1]Roux and Dhanarajan, 1990, which disclosure is HEREBY incorporated by reference.
[2]Parentheses indicate a mixture of the nucleotides; N indicates a mixture of all 4 nuclotides.
[3]Indicates priming of synthesis of the coding (+) or complementary (−) DNA strand.

These primer pools comprise all possible sequences (+ strand) encoding the first seven amino acids of a conserved octapeptide (TTVLTMTT (SEQ. ID. NO. 1) ) sequence element found in the second transmembrane domain (M2) of most known ligand-gated chloride channel genes. The second primer site was provided by ligation of an oligonucleotide adapter comprised of a tailed linker and an anchor template (Table 1) to Drosophila. melanogaster (Canton-S) genomic DNA digested to completion by BamH1 or BglII. Initial single strand synthesis was primed only by TP1a, TP1b, or TP1c, whereas subsequent cycles of amplification were primed by both the target primer and the anchor primer (AP). In this approach, selective geometric amplification occurs because the AP anneals only to DNA complimentary to the anchor template that is formed in the first strand synthesis. PCR reactions (50 μl) included 50 ng template prepared as above, 200 μM TP1a, TP1b, or TP1c, 2 mM AP, 250 μM dNTP's, 50 mM KCl, 10 mMTris-HCl (pH 8.8), 1.5 mM MgCl$_2$, 0.1% Triton X-100, 1 U Taq DNA polymerase (Perkin Elmer Cetus) and 0.5 U Perfect Match (Stratagene). Thirty-five cycles of amplifications were performed using the following cycle program: denaturation for 1 minute at 94° C., annealing for 1 minute at 52° C., and extension at 72° C. for 0.5 minutes. DNA amplification products were detected by electrophoresis of 10 μl of the reaction in 3% Nusieve GTG/1% Seakem ME (FMC) agarose gels, followed by ethidium bromide staining.

The second homology probing procedure employed two degenerate primers, TP2 (Table 1) and either TP1a, TP1b, or TP1c. The 256-fold degenerate TP2 comprises all possible sequences (− strand) that encode the CFVFVF (SEQ.ID.NO.28) motif, which is conserved in the third transmembrane domain (M3) of GABA receptor β subunit sequences (Harvey et al., 1991, cited elsewhere herein, which disclosure is hereby incorporated by reference). Reactions were performed under similar conditions to those described above, except that TP2 (100 μM) was used instead of AP, unmodified genomic DNA was used as the template, and the reactions were carried out with the following program: denaturation for 50 seconds at 92° C., annealing for 30 seconds at 45° C. (first 5 cycles) or 52° C. (last 30 cycles), and extension for 30 seconds at 72° C.

To facilitate subcloning of the products obtained from the single site PCR method an XbaI restriction site was incorporated at the 5' end of TP1a, TP1b or TP1c. Amplification products were digested with XbaI after precipitation from the reaction mix with ethanol. The XbaI-digested products were excised from 0.8% to 2.0% Seaplaque GTG (FMC) low melting temperature aqarose gels following electrophoresis in TAE buffer, and ligated with T4 DNA ligase (Promega) directly to XbaI- and SmaI-digested pBluescript KS+ plasmid DNA (Stratagene). The major product obtained by the standard PCR method was similarly isolated by cutting with XbaI and EcoRI at the restriction sites incorporated into the oligonucleotide primers and ligation into XbaI and EcoRI-digested pBluescript KS+ plasmid DNA. E. coli host strain XL1-Blue (Stratagene) was transformed with the in-gel ligation mixtures and individual transformant colonies were screened for the presence of insert-containing plasmids by PCR (Zon et al., 1989, *Biotechniques*, vol. 7, pp. 696–698, which disclosure is hereby incorporated by reference).

2. Recombinant Bacteriophage Library Screening:

$^{32}$P-Labelled probes were prepared using linearized plasmid DNAs containing the subcloned PCR products as templates in Taq Polymerase-mediated primer extension reactions. The reaction mixture (50 μl) contained 50 mM KCl, 10 mMTris-HCl (pH 8.8), 1.5 mM MgCl$_2$, 0.1% Triton X-100, 1 U Taq Polymerase (Promega), 20 μM dATP, dGTP, and dTTP, 2 μM dCTP, 200 μCi of 6000 Ci/mmol [α-$^{32}$P]dCTP (NEN), 1 μg plasmid DNA, and 0.5 μM primer. Reaction mixtures were incubated for 50–60 cycles according to the following program: denaturation for 50 seconds at 92° C., annealing for 30 seconds at 52°–60° C. (depending on primer), and extension for 30 seconds at 72° C. Unincorporated [α-$^{32}$P]dCTP was removed from the probe by chromatography using a G50 sephadex (Pharmacia) column. A λ EMBL4 library containing *Drosophila melanogaster* (Canton-S) genomic DNA (Knipple et al., 1991, cited elsewhere herein, which disclosure is hereby incorporated by reference) was transferred to nitrocellulose (Millipore) using the plaque lift procedure (Benton et al., 1977, *Science*, vol. 196, pp. 180–192, which disclosure is hereby incorporated), and screened by hybridization overnight at 43° C. in 4 ml hybridization buffer (50% formamide, [5X] Denhardt's solution, 0.1% SDS, [6X]SET, 100 μg/ml calf thymus DNA (Sigma), and 20 μCi purified probe). The final high stringency wash was in [0.2X]SET and 0.1% SDS for 1 hour at 67° C. Following plaque purification, phage DNA was extracted and purified by standard methods (Maniatis et al., 1982, Cold Spring Harbor Laboratories, Cold Spring Harbor, N.Y., which disclosure is hereby incorporated). Restriction fragments of the genomic DNA clones obtained in these procedures were identified by Southern analysis with the same probe and subcloned into pBluescript KS+ or KS− plasmid DNA.

3. DNA Sequence Analysis:

Double stranded plasmid templates were isolated by the alkaline lysis procedure (Birnboim, H. C., 1983, *Meth. Enzymol.*, vol. 100, pp. 243–255, which disclosure is hereby incorporated), followed by PEG precipitation. Single stranded templates from XL1-Blue cells were isolated as recommended by Stratagene. All DNA sequencing was based on the dideoxynucleotide termination procedure (Sanger et al., 1977, *Proc. Natl. Acad. Sci. USA*, vol. 74, pp. 5463–5467, which disclosure is hereby incorporated), adapted for either $^{35}$S labelling and autoradiography or dye labelling for use with an Applied Biosystems Model 373 Automated DNA Sequencer. Open reading frames were searched for intron splice junctions by a combination of the following computer-aided sequence analysis approaches: 1) identification of consensus splice junction nucleotide sequences; 2) comparisons to available cDNA sequences; and 3) identification of divergence in deduced amino acid sequence from those in conserved regions of previously cloned gene family members.

4. Cytogenetic Localization of Cloned DNAs:

The cytogenetic location of each cloned DNA was determined by in situ hybridization to polytene chromosome preparations from third instar larval salivary glands using a standard procedure (Pardue et al., 1975, *In Methods in Cell Biology* (Edited by D. P. Prescott), vol. 10, pp. 1–16, which disclosure is hereby incorporated by reference) modified for use of biotinylated probes. Salivary glands were dissected from third instar larvae of the Canton S strain and polytene chromosome spreads prepared as described previously (Knipple et al., 1991, cited elsewhere herein, which disclosure is hereby incorporated by reference). Recombinant bacteriophage DNA was labeled by the mixed primer labeling procedure (Feinberg et al., 1983, *Anal. Biochem.*, vol. 132, pp. 6–13, which disclosure is hereby incorporated by reference) using biotin-21-dUTP (Clontech) according to the protocol of the supplier. The biotinylated probe was ethanol precipitated in the presence of tRNA carrier and resuspended in 40 μl of hybridization solution that was 0.6M NaCl, 50 mM sodium phosphate, pH 8.0, [1X] Denhardt's solution (0.02% BSA/0.02% Ficoll/0.02% polyvinylpyrrolidone), 4 mg/ml of carrier tRNA, and 5 mM MgCl$_2$. Each slide containing chromosome spreads was heat-treated and denatured immediately prior to the addition of 10 μl of denatured hybridization solution. Hybridization was performed at 58° C. for 48 hours after which the following wash sequence was performed: three washes for 15 minutes at 53° C. in [2X] SSC, two for 5 minutes in [1X] PBS at room temperature, and a brief rinse in [1X] PBS/0.1% Triton X-100. The hybridized and washed chromosome preparations were then incubated for 1 hour at 37° C. with 100 μl of 0.5% (v/v) Detek streptavidin/horseradish peroxidase conjugate (Enzo) in [1X] PBS/0.1% Triton X-100. Following three 5 minutes washes in [1X] PBS at room temperature, signal was developed by incubation for 1 hour at 37° C. with 100 ml of 54 (w/v) diaminobenzidine (Sigma), 1% hydrogen peroxide in [1X] PBS/0.1% Triton X-100. Following a brief rinse in [1X] PBS and counter-staining with Giemsa for 30 seconds, orange-brown (lighter signal) to black stain deposition corresponding to sites of hybridization were detected visually as narrow bands against the background of light blue chromosome staining. Photomicrographs of labeled sites were made at 1000X amplification through differential interference contrast (Nomarski) optics using an Olympus BH-2 Microscope, Kodak Technical Pan 2415 film, and an Olympus PM-10ADS photomicrographic system.

5. Screening Of Recombinant Bacteriophage Libraries:

The *Drosophila melanogaster* cDNA libraries used were constructed in λgt10 and correspond to mRNAs isolated from discrete embryonic, larval, and pupal developmental stages as described by Poole et al., 1985, *Cell*, vol. 40, pp. 37–43, which disclosure is hereby incorporated by reference. A genomic library was made in λEMBL4 with DNA form a Canton S strain according to the procedures of Knipple et al., 1991, cited elsewhere herein, which disclosure is hereby incorporated by reference. To identify cDNA libraries containing β-subunit-specific sequences, phage DNA was prepared from plate lysates of each library by a rapid small scale procedure as described by Benson et al., 1984, *Biotechniques*, vol. 2, pp. 126–27, which disclosure is hereby incorporated by reference and used as the template for PCR reactions (Saiki et al., 1988, Science, vol. 239, pp. 487–491 which disclosure is hereby incorporated by reference) employing oligonucleotide primers designed to amplify GABA receptor β-subunit-specific sequences as previously described. Libraries were plated and transferred in duplicate to nitrocellulose (Millipore) using the plaque lift procedure as described by Benton et al., 1977, cited elsewhere herein, which disclosure is hereby incorporated by reference, and hybridized overnight with $^{32}$P-labelled proves at 43° C. in 50% formamide, 5X Denhardt's solution, o.1% SDS, 6X SET, 100 µg/ml calf thymus DNA, and 20 µCi purified probe.

To prepare high specific activity probes, 50 cycles of Taq polymerase-mediated primer extension were performed using a 266 kb gel-purified fragment of coding sequence (derived from a 2.26 kb LCCH3 genomic subclone) as template and specific primers directing the synthesis of either sense or antisense strands (5'-GCCGCAGTTCAC-CATCATTG-3'(SEQ. ID. NO. 11) and 5'-AGTGAGCTGC-GAACACCCGTG-3'(SEQ. ID. NO. 12), respectively). Labelling reactions (50 µl) contained 50 mM KCl, 10 mM Tris-HCl (pH 8.8), 1.5 mM MgCl$_2$, 0.1% Triton X-100, 1 U Taq DNA Polymerase, 20 µM each dATP, dGTP, and dTTP, 2 µM dCTP, 200 µCi of 6000 Ci/mmol [α-$^{32}$P]dCTP (NEN), 100 ng template DNA, and 0.5 µM primer. Unincorporated [α-$^{32}$P]dCTP was removed by elution over a G50 Sephadex (Pharmacia) column. One set of transfers was hybridized with the sense strand probe, and the duplicate set was hybridized with the antisense strand probe. The final high stringency post-hybridization wash was in 0.2X SET and 0.1% SDS for 1 hour at 67° C. Probe-positive plaques were purified and the cDNA or genomic inserts subcloned into pBluescript SK+ plasmid DNA (Stratagene) using standard techniques (Sambrook et al., Molecular Cloning: A laboratory Manual, 1989, Cold Spring Harbor Laboratory Press, which disclosure is hereby incorporated by reference).

6. PCR Amplification Of The cDNA 3' End:

Comparison of the DNA sequences of the isolated cDNA and the LCCH3 genomic DNA indicated that the former was truncated at its 3' end by approximately 500 bp due to the occurrence of an A-rich stretch of sequence in the coding region. In order to isolate the 3' end of the LCCH3 mRNA expeditiously, the pupal cDNA library was used as a template in PCR using primers selected on the basis of sequences from the LCCH3 genomic subclone. The downstream-directed primer (5'-TTTCGTGTTCGCAGC-CCTCT-3' (SEQ.ID.NO.13)) was designed to be identical to the sense strand of the DNA coding for the -VFVFAAL- (SEQ. ID. NO. 29) amino acid sequence motif in the putative transmembrane domain M3. The upstream-directed primer (5'GGTCTAGAAGTCAATCTTTATTATGGAGG-3'(SEQ.ID.NO.14)) was designed to be identical to the complementary strand adjacent to a putative polyadenylation site located 106 bp downstream of the apparent termination signal, which was identified on the basis of the consensus polyadenylation signal (AATAAA) (SEQ. ID. NO. 30) followed by CA 14 bases downstream, with no other CA motifs nearby (Wahle et al., 1992, *Annu. Rev. Biochem.*, vol. 61, pp. 419–440, which disclosure is hereby incorporated by reference). PCR reactions (50 µl) included 50 ng cDNA template, 0.5µM of each primer, 250 mM dNTP's, 50 mM KCl, 10 mMTris-HCl (pH 8.8), 1.5 mM MgCl$_2$, 0.1% Triton X-100, 1 U Taq Polymerase (Perkin elmer Cetus) and 0.5 U Perfect Match (Stratagene). Amplifications were performed using 35 cycles on a Techne PHC-1 thermal cycler using the following cycle program: denaturation for 1 minute at 94° C., annealing for 1 minute at 56° C., and extension for 0.5 minutes at 72° C. DNA amplification products were detected by electrophoresis of 10 µl of the reaction in 3% Nusieve GTG/1% Seakem ME (FMC) agarose gels, followed by ethidium bromide staining.

7. DNA Sequence Analysis:

DNA sequencing was performed using the dideoxynucleotide chain termination procedure as described by Sanger et al., 1977, cited elsewhere herein, which disclosure is hereby incorporated by reference, adapted for either $^{35}$S labelling with Sequenase and autoradiography or dye terminator labelling with Taq polymerase and automated sequencing using an Applied Biosystems Model 373 Automated DNA Sequencer. Templates for DNA sequencing were either: plasmid DNA isolated by the alkaline lysis procedure (Birnboim, 1983, cited elsewhere herein, which disclosure is hereby incorporated by reference), followed by PEG precipitation; single-stranded pBluescript DNA isolated by a standard method (Vieira et al., 1987, *Method. Enzymol.*, vol. 153, pp. 3–11, which disclosure is hereby incorporated by reference) with modification as recommended by Stratagene for XL1-Blue cells; or linear DNA fragments synthesized by performing an additional 25 cycles of PCR on gel-purified PCR products, followed by purification in a Centicon-100 (Amicon) filtration device. DNA sequence comparisons were made using the Genetics Computer Group on BioVAX and MacVector (IBI) software.

EXAMPLE II

PCR-BASED HOMOLOGY SCREENING

PCR-based homology screening of *Drosophila melanogaster* genomic DNA with degenerate oligonucleotide primers was conducted (Gould et al., 1989, *Proc. Natl. Acad. Sci. USA*; , vol. 86, pp. 1934–9138; and Kamb et al., 1989, *Proc. Natl. Acad. Sci. USA*, vol. 86, pp. 4372–4376, which disclosures are hereby incorporated by reference) to amplify genomic sequences that encode the first seven amino acids of an octapeptide (TTVLTMTT)(SEQ.ID.NO.1) "signature motif," which is conserved in the M2 region of most of the characterized ligand-gated chloride channel genes. Using the single site PCR strategy, seven amplification products were obtained that ranged in size from approximately 100 to 300 bp from reactions employing the three target primer pools and either BglII- or BamHI-cut and anchor-adapted

*Drosophila melanogaster* genomic DNA. Sequence analysis of the subcloned PCR products revealed that two of these sequence elements (designated LCCH1 and LCCH2) contained extended open reading frames having greater than 40% identity of their predicted amino acid sequences to the corresponding sequences encoded by vertebrate ligand-gated chloride channel subunit genes in this highly conserved region. The other five products had very short open reading frames or little similarity to ligand-gated chloride channel genes outside of the target sequence for PCR primer design.

EXAMPLE III

PCR HOMOLOGY PROBING

A PCR homology probing strategy was conducted, with degenerate target primers specifying two defined sequence elements, in a search for *Drosophila melanogaster* genomic fragments with GABA receptor β subunit-like sequences. This strategy yielded a single product (designated LCCH3) when TP1b was used as the downstream-directed target primer pool, but did not yield other products with either the TP1a or TP1c primer pools. LCCH3 contained an extended open reading frame, and the predicted amino acid sequence of this fragment exhibited greater than 40% identity to the corresponding sequences encoded by GABA receptor B subunit genes. A similar strategy was employed to search for GABA receptor α subunit-like sequences, based on the ATVNYFT (SEQ.ID.NO.31) amino acid sequence motif present in M3 of all vertebrate α subunits, but a specific amplification product using the α subunit-specific primer in combination with any of the three TP1 primer pools was not observed.

EXAMPLE IV

CHARACTERIZATION OF TRANSCRIPTION UNITS

To further characterize the transcription units from which the LCCH1, LCCH2, and LCCH3 amplification products were derived, approximately 60,000 plaques were screened from a *Drosophila melanogaster* genomic library, and isolated clones identified by each probe. Southern analysis of restriction digests from one of each group of genomic clones identified the following fragments that were used in subsequent analysis: 1) a 2 kb BamHI/HindIII fragment of LCCH1; 2) a 1.7 kb EcoRI/BglII fragment of LCCH2; and 3) a 2.3 kb XbaI/EcoRI fragment of LCCH3. Sequencing of the regions flanking the original amplified segments of these DNAs provisionally identified the LCCH1, LCCH2, and LCCH3 transcription units as members of the ligand-gated chloride channel gene family of *Drosophila melanogaster* based on the conservation of several distinctive features of the amino acid sequences encoded by open reading frames of each genomic fragment. To illustrate these homology relationships, the deduced amino acid sequences of these clones in the putative M2–M3 regions are shown in FIG. 1 along with those of previously characterized representative ligand-gated chloride channel genes. With reference to FIG. 1, the expanded M2–M3 region is represented by the single letter amino acid code for putative Drosophila ligand-gated chloride channel homologues LCCH1, LCCH2, and LCCH3 and representative established gene family members. α1, β1, γ2, and δ are: bovine α1 and β1 (Schofield et al., 1987, cited elsewhere herein, which disclosure is hereby incorporated by reference); and rat γ2 and δ (Shivers et al., 1989, *Neuron*, vol. 3, pp. 327–337, which disclosure is hereby incorporated by reference) GABA receptor subunits. Lym β is the Lymnaea GABA receptor β subunit (Harvey et al., 1991, cited elsewhere herein, which disclosure is hereby incorporated by reference). Glα is the rat α1 glycine receptor subunit (Grenningloh et al., 1987, *Nature*, vo. 328, pp. 215–220, which disclosure is hereby incorporated by reference). Amino acids that are conserved in all sequences are shown in boldface type. Dashes in the LCCH1 sequence identify the point of divergence of this fragment from the corresponding cDNA sequence (ffrench-Constant et al., 1991, cited elsewhere herein, which disclosure is hereby incorporated by reference). The DNA sequence obtained for the LCCH1 coding region was delimited by a Sau3AI subcloning site, which occurred just upstream of the conserved M2 sequence motif, and by an intron-exon splice junction near the downstream end of M3. Although only the putative M2–M3 regions of LCCH2 and LCCH3 are shown in FIG. 1, the open reading frames of both these clones extended beyond M2 upstream and beyond M3 downstream, as explained hereinafter and shown in FIG. 3.

EXAMPLE V

CONSERVED *DROSOPHILA MELANOGASTER* SEQUENCES

The following elements, which are conserved in other members of this gene family, were found to be conserved across all three *Drosophila melanogaster* sequences ( i.e., LCCH1, LCCH2, LCCH3): 1) invariant Arg and Gly residues in proper alignment in M2; 2) the first seven amino acids of the octapeptide signature motif; 3) the invariant Leu-Pro motif in the extracellular loop between M2 and M3; and 4) invariant Asp and Phe residues in proper alignment in M3. LCCH1 and LCCH3 contained the full octapeptide signature motif in M2, but LCCH2 showed a substitution of Phe for Thr in the eighth residue. Each *Drosophila melanogaster* fragment also contained other sequence elements that were conserved in comparison with some of the known ligand-gated chloride channel genes but were not invariant across the entire family. Hydropathy plots (not shown) of the predicted amino acid sequences deduced from the open reading frames of LCCH1, LCCH2, and LCCH3 were similar to those derived for the corresponding regions of other characterized ligand-gated chloride channel subunit genes, and showed highly hydrophobic segments corresponding to the inferred M2 and M3 regions separated by a short hydrophilic segment.

EXAMPLE VI

AMINO ACID SEQUENCES

Paired comparisons of inferred amino acid sequences in the M2–M3 region (Table 2) showed that LCCH1 and LCCH3 were more similar to each other (68% amino acid identity) than either was to LCCH2 (46% and 49% amino acid identity, respectively).

TABLE 2[1]

|       | LCCH2 | LCCH3 | Lym β | α1 | β1 | γ2 | δ  | Glα |
|-------|-------|-------|-------|----|----|----|----|-----|
| LCCH1 | 46    | 68    | 68    | 49 | 65 | 49 | 60 | 61  |
| LCCH2 | —     | 49    | 49    | 46 | 47 | 46 | 47 | 49  |
| LCCH3 | —     | —     | 96    | 49 | 79 | 60 | 65 | 72  |
| Lym β | —     | —     | —     | 49 | 79 | 58 | 63 | 70  |
| α1    | —     | —     | —     | —  | 49 | 65 | 54 | 60  |

TABLE 2[1]-continued

|    | LCCH2 | LCCH3 | Lym β | α1 | β1 | γ2 | δ  | Glα |
|----|-------|-------|-------|----|----|----|----|-----|
| β1 | —     | —     | —     | —  | —  | 56 | 56 | 67  |
| γ2 | —     | —     | —     | —  | —  | —  | 63 | 63  |
| δ  | —     | —     | —     | —  | —  | —  | —  | 58  |

[1]Identifies all calculated from the data shown in FIG. 1 (See FIG. 1 for abbreviations and references to published sequences).

In comparisons with other members of this gene family in the M2–M3 region, LCCH1 was most similar to the Lymnaea and rat GABA receptor β subunits and the α subunit of the rat glycine receptor. LCCH3 exhibited a very high degree of sequence identity to the Lymnaea β subunit (96%) and considerable sequence identity with the rat GABA receptor β subunit (79%). In contrast, LCCH2 exhibited only 46% to 49% sequence identity in the region in pairwise comparisons with all other sequences.

EXAMPLE VII

CYTOGENETIC LOCATIONS

Figure 2:
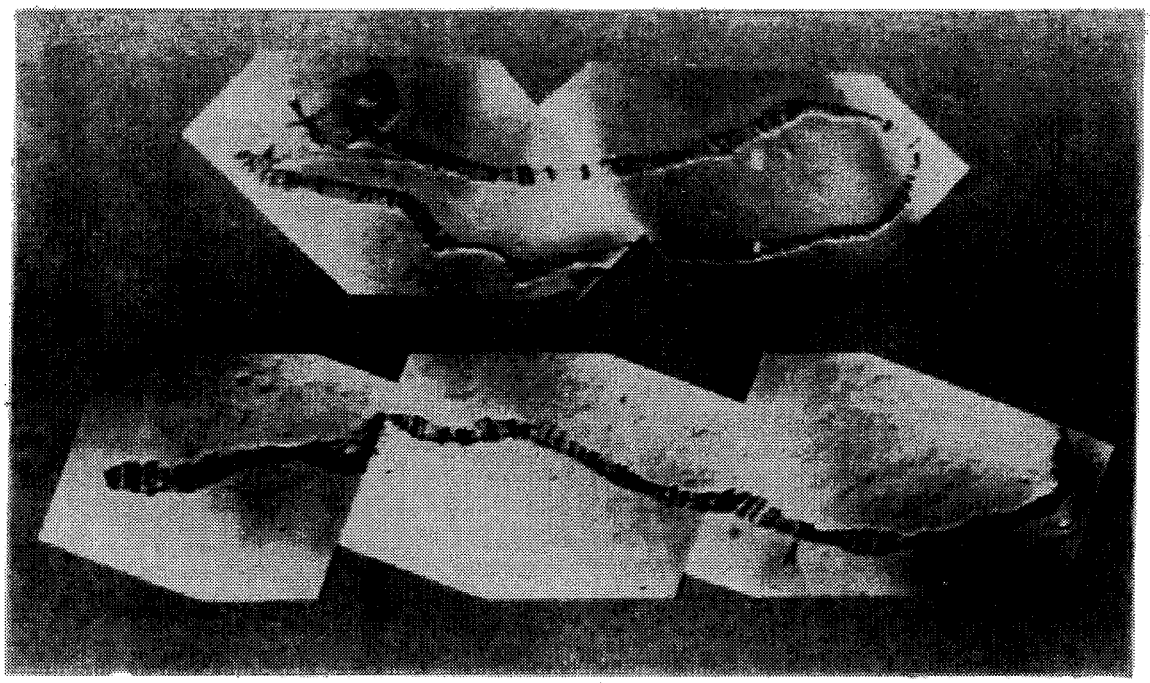
FIG. 2 is a composite photomicrographs of *Drosophila melanogaster* polytene chromosomes labelled with biotinylated DNA probes (Top: left arm of chromosome 3 showing labelling (arrow) of cytogenetic region 75A by a LCCH2 probe; Bottom: X chromosome showing labelling (arrow) of cytogenetic region 13F by a LCCH3 probe).

The cytogenetic locations of the cloned LCCH1, LCCH2, and LCCH3 genomic DNAs were determined by hybridizing biotinylated probes prepared from each sequence to Drosophila melanogaster polytene chromosome squashes in situ. The LCCH1 probe labelled cytogenetic region 66F on the left arm of chromosome 2 (not shown), a finding consistent with the known location of Rdl (=LCCH1) to 66F (ffrench-Constant et al., 1991, cited elsewhere herein, which disclosure is hereby incorporated by reference). The LCCH2 probe labelled cytogenetic region 75A on the left arm of chromosome 3 (FIG. 2, top). The LCCH3 probe labelled cytogenetic region 13F on the X chromosome (FIG. 2, bottom).

EXAMPLE VIII

Isolation and Sequencing Of Genomic DNA:

The use of PCR-based homology probing to identify novel LCCHs elements in the Drosophila melanogaster genome, provisionally designated LCCH1, LCCH2, and LCCH3, permitted isolation of corresponding genomic DNA clones. Sequencing of a 2.3 kb XbaI/EcoRI restriction fragment of the LCCH3 genomic clone (data not shown) identified three open reading frames encompassing 987 bp, which encode amino acid sequences having high homology in regions corresponding to the four transmembrane domains (M1–M4) of GABA receptor β subunits of vertebrates (Schofield et al., 1987, Nature, vol. 328, pp. 221–227; and Ymer et al., 1989, EMBO/J., vol. 6, pp. 1665–70, which disclosures are hereby incorporated by reference) and Lymnaea stagnalis (Harvey et al., 1991, cited elsewhere herein, which disclosure is hereby incorporated by reference).

EXAMPLE IX cDNA Isolation and Sequencing:

In preliminary PCR-based screens of embryonic and pupal cDNA libraries, LCCH3-homologous sequences, identified by the presence of a predicted 134 bp amplification product, were detected only in the pupal library. A single 1.65 kb cDNA clone was isolated by screening approximately 850,000 plaques form this library using a hybridization probe derived form the M1–M3 transmembrane encoding region of the 2.3 kb XbaI/EcoRI genomic DNA restriction fragment. Sequencing of this clone revealed an open reading frame extending downstream from a putative translation initiation site near the 5' end to the 3' end of the clone. Comparison of this sequence to that of the 2.3 kb genomic subclone revealed that the cDNA clone was truncated at the 3' end in an adenosine-rich motif in the M3 domain, but was otherwise identical to two upstream exons identified on the genomic subclone. The availability of genomic DNA sequence, which identified both the cDNA truncation site and the 3' end of the transcription unit, permitted the design of PCR primers for the specific amplification of the 3' end of the cDNA from the pupal cDNA library. Thus, the complete coding sequence of LCCH3, comprising a single open reading frame of 1488 nucleotides (FIG. 4), was deduced from the 1.65 kb cDNA clone and an overlapping 615 bp amplification product having a nucleotide sequence identical to the downstream open reading frames identified in the LCCH3 genomic DNA, and corresponding to the 3' end of the gene. With reference to FIG. 4, the nucleotide sequence (SEQ.ID.NO.3) is numbered arbitrarily from the first ATG open reading frame. The amino acid sequence (SEQ.ID.NO.2) is numbered from the first residue of the predicted mature polypeptide. Amino acids in the putative signal sequence are given negative numbers. Conserved cysteine residues in the extracellular domain are marked with asterisks, and the four inferred hydrophobic transmembrane domains are underlined.

EXAMPLE X

Figure 5:
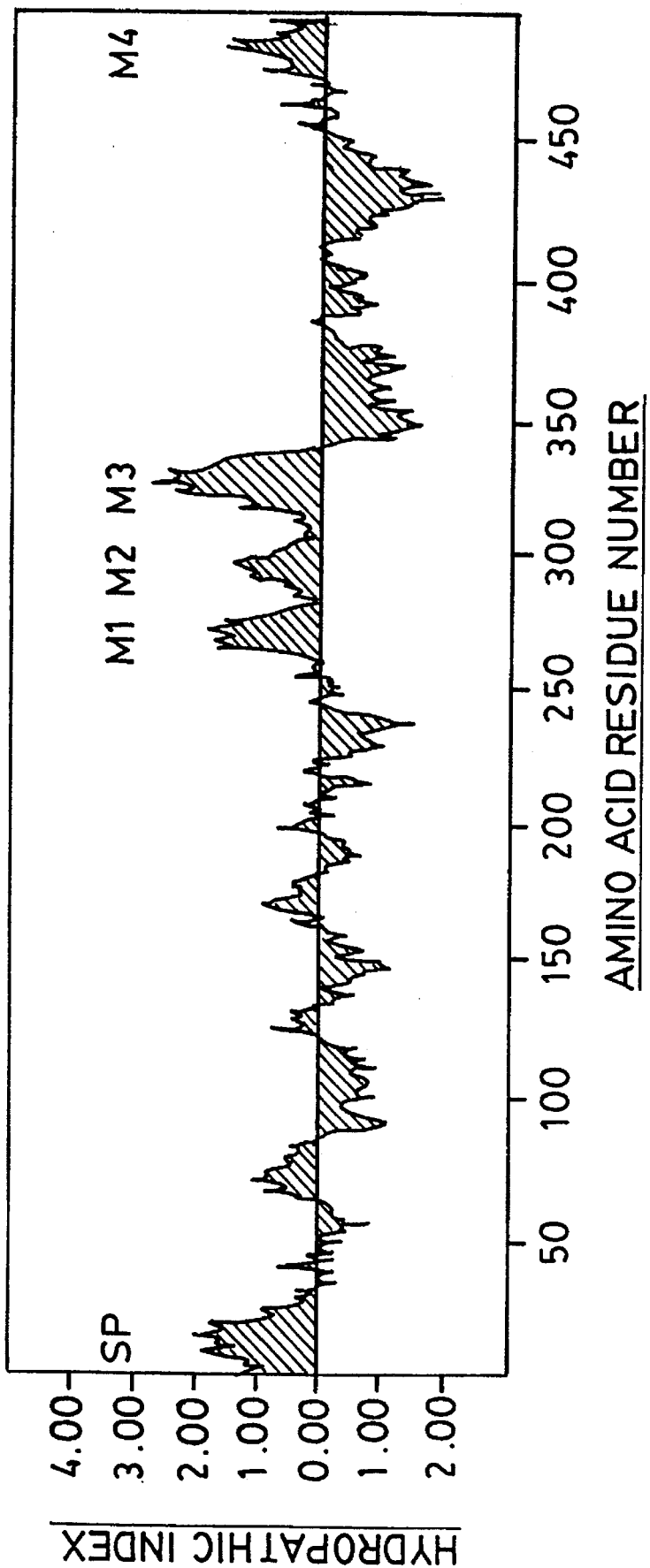
FIG. 5 is a hydropathy profile of the LCCH3 gene product calculated with a window size of 17 residues.

Structural Analysis Of The Inferred Amino Acid Sequence:

The LCCH3 cDNA encodes a 496-amino acid polypeptide (FIG. 4, SEQ.ID.NO.2). The hydropathy profile of the predicted gene product, illustrated by FIG. 5, shows five extended hydrophobic domains: one at the 5' end of the open reading frame forming a putative signal peptide sequence and four in the 3' half of the sequence corresponding to putative transmembrane domains. With reference to FIG. 5, the putative signal peptide sequence (SP) and transmembrane domains (M1–M4) are indicated. Both the relative position and the amino acid sequences of the four transmembrane domains are conserved with respect to other known members of the ligand-gated chloride channel gene family (FIG. 6).

With reference to FIG. 6, the alignment of the predicted amino acid sequence of the present isolated gene fragment (LCCH3, SEQ.ID.NO.2) with those of the Lymnaea stagnalis GABA receptor β-like subunit (SEQ.ID.NO.24)(Harvey et al., 1991, cited elsewhere herein, which disclosure is hereby incorporated by reference), the rat GABA receptor β1 subunit (SEQ.ID.NO.25) (Birnboim, H. C., 1983, cited elsewhere herein, which disclosure is hereby incorporated by reference), and the Drosophila melanogaster Rdl locus (SEQ.ID.NO.26)(ffrench-Constant et al., 1991, cited elsewhere herein, which disclosure is hereby incorporated by reference) using the GCG computer program is illustrated. All sequences are numbered from the first residue of the mature polypeptide, and putative signal sequence residues are given negative numbers. Amino acids that are identical in all four sequences are enclosed in boxes. The putative extracellular disulfide-bridged loop structure is underlined with a dotted line, and the four hydrophobic transmembrane domains are underlined with solid lines. The predicted mature gene product after signal peptide cleavage (von Heijne, G., 1986, *Nucl. Acids Res.*, vol. 14, pp. 683–4690, which disclosure is hereby incorporated by reference) is a 476-amino acid polypeptide with a molecular weight of 54,442 daltons. The large N-terminal extracellular domain of this polypeptide contains a conserved 15-amino acid sequence element (amino acid residue 152–166) bounded by cysteine residues (Cys152 and Cys166) capable of forming the disulfide-bridged loop found in the extracellular domain of all members of the ligand-gated ion channel gene superfamily (Barnard et al., 1987, cited elsewhere herein, which disclosure is hereby incorporated by reference). The extracellular domain also contains two possible sites for N-linked glycosylation, Asn19 and Asn169, (Kornfeld et al., 1985, *Annu. Rev. Biochem.*, vol. 54, pp. 931–964, which disclosure is hereby incorporated by reference). None of the putative intracellular domains of the predicted polypeptide contain a consensus recognition sequence (RRXSX) (SEQ.ID.NO.27) for phosphorylation by cAMP-dependent protein kinase, but the large intracellular domain contains two phosphorylation sites (Ser368 and Ser434) with alternative recognition sequences (Kemp et al., 1990, Trends Biochem. Sci., vol. 15, pp. 342–346, which disclosure is hereby incorporated by reference).

RESULTS

Both the nervous system and neuromuscular junctions of insects contain ligand-gated chloride channels (Lummis et al., 1990, cited elsewhere herein; and Sattelle, D. B., 1990, cited elsewhere herein, which disclosures are hereby incorporated by reference) that may be encoded by homologues of the ligand-gated chloride channel genes that have been described for vertebrates and molluscs. Despite the availability of cloned cDNAs of mammalian ligand-gated chloride channel subunit genes, there are no reports of the successful use of these cDNAs as probes for the isolation of homologous genes from insects. The existence of a short stretch of invariant amino acids (TTVLTMTT)(SEQ.ID.NO.1) in the second inferred transmembrane domain of all reported vertebrate ligand-gated chloride channels except for the GABA ρ subunit (Cutting et al., 1991, *Proc. Natl. Acad. Sci. USA*, vol. 88, pp. 2673–2677, which disclosure is hereby incorporated by reference) led us to hypothesize that this octapeptide might be a conserved "signature motif" for the ligand-gated chloride channel gene family and therefore might be present in homologous insect ligand-gated chloride channels.

This hypothesis was tested by PCR-based homology probing, employing degenerate primer pools coding for the first seven amino acids of the signature motif. The existence in this gene family of only a single stretch of invariant amino acid sequence long enough for PCR primer design necessitated the use of a single site PCR approach (Roux et al., 1990, cited elsewhere herein, which disclosure is hereby incorporated by reference), which yielded a set of seven unique genomic fragments containing this motif. Within this set were two fragments (LCCH1 and LCCH2) with extensive open reading frames and considerable homology to established ligand-gated chloride channel genes. It is likely that other members of this sequence family exist in *Drosophila melanogaster* but were not identified in the present experiments because the single site PCR-based search was limited to those genes with BglII or BamHI restriction sites downstream of the signature motif and within range of PCR amplification under the specific reaction conditions that we employed. A more thorough single site search would include the use of other restriction sites in the digestion and modification of template DNA, upstream-directed primers based on the TTVLTMTT (SEQ.ID.NO.1) motif, and variations of the TTVLTMTT (SEQ.ID.NO.1) motif (Cutting et al., 1991, cited elsewhere herein, which disclosure is hereby incorporated by reference).

A supplementary approach was designed to probe specifically for GABA β receptor subunit-like sequences. This strategy was based on the presence of a conserved CFVFVF (SEQ.ID.NO.28) motif in the third transmembrane domain of both vertebrate and molluscan GABA receptor β subunits (Harvey et al., 1991, cited elsewhere herein, which disclosure is hereby incorporated by reference). When degenerate primers directed toward the CFVFVF (SEQ.ID.NO.28) motif were employed together with the available pools of primers for the octapeptide motif in conventional PCR amplifications, a single PCR product (LCCH3) was obtained with striking homology to the molluscan GABA receptor β subunit. This finding provides evidence for a larger family of ligand-gated chloride channel sequence elements in the *Drosophila melanogaster* genome (identified in original homology probing strategy). However, a similar approach directed toward the isolation of GABA α receptor subunit-like sequences, based only on vertebrate sequence information, was not successful.

The predicted amino acid sequences of the three *Drosophila melanogaster* genomic fragments was compared to assess the degrees of relatedness among these fragments and other genes in this family (Table 2). The comparisons were restricted to the presumptive M2 and M3 domains because sequence data with open reading frames corresponding to these regions were available for all three *Drosophila melanogaster* sequence elements. The M2 and M3 domains contain amino acid sequence elements that are conserved across all known members of the gene family as well as elements characteristic of each GABA receptor subunit class. In this region, ligand-gated chloride channel gene family members all have greater than 40% amino acid identity to each other but share less than 20% identity with more distantly related members of the ligand-gated ion channel gene superfamily (Schofield et al., 1987, cited elsewhere herein, which disclosure is hereby incorporated by reference).

LCCH1 shares 100% amino acid and nucleotide sequence identity in the M2-M3 region with the *Drosophila melanogaster* cDNA from the Rdl locus (ffrench-Constant et al., 1991, cited elsewhere herein, which disclosure is hereby incorporated by reference). Comparison of the sequences of LCCH1 and the homologous cDNA identified an apparent exon/intron splice junction at Glu353 of the cDNA. This finding is in agreement with a recent report describing the intron-exon splice junction locations for the Rdl locus (ffrench-Constant et al., 1992, cited elsewhere herein, which disclosure is hereby incorporated by reference). The identification of Rdl (=LCCH1) as a GABA receptor subunit is based on both the inferred structure and the functional expression of the Rdl gene product (ffrench-Constant et al., 1991; ffrench-Constant et al., 1993, *Nature*, vol. 363, pp. 449–451, which disclosure is hereby incorporated by reference).

In contrast to LCCH1, both LCCH2 and LCCH3 represent previously undescribed genes in *Drosophila melanogaster*. Comparisons of amino acid sequence in the M2-M3 region between LCCH2 and established ligand-gated chloride channel genes showed that LCCH2 contains the invariant landmarks of this gene family with the notable exception that the octapeptide motif is truncated by the replacement of the terminal Thr with Phe. The predicted amino acid sequence of LCCH2 in this region is equally divergent from all other known sequences in the gene family. This result suggests that LCCH2 may represent a novel class of GABA receptor subunit or may encode a subunit of a ligand-gated chloride channel that is gated by an agonist other than GABA. Such genes are implicated to exist by the physiological evidence for distinct glutamate-, taurine-, and histamine-gated chloride channels in insects (Lummis et al., 1990, cited elsewhere herein, which disclosure is hereby incorporated by reference).

Results of in situ hybridization experiments show that LCCH2 is located at cytogenetic region 75A. A Drosophila melanogaster genomic DNA clone isolated with a rat glycine receptor α subunit cDNA probe has also been reported to map onto this region, but there is no reported mutation mapping to this cytogenetic interval that might provide insight into the physiological function of the LCCH2 gene product (Lindsley et al., 1992, *The genome of Drosophila melanogaster*, Academic Press, New York, which disclosure is hereby incorporated by reference).

LCCH3 exhibited 96% amino acid sequence identity to the established molluscan GABA receptor β subunit (Harvey et al., 1991, cited elsewhere herein, which disclosure is hereby incorporated by reference) in the putative M2 and M3 domains, a degree of sequence identity comparable to that shared between subunit isomorphs in vertebrates. Moreover, sequence analysis of the entire 501-nucleotide open reading frame of the genomic subclone corresponding to LCCH3 showed a high degree of sequence identity between LCCH3 and the molluscan GABA receptor β subunit upstream from the region of comparison through M1 and into the presumed extracellular domain (data not shown). Thus, LCCH3 appears to represent the homologue in *Drosophila melanogaster* of the molluscan GABA receptor β subunit. This conclusion is supported herein by the determination of the complete LCCH3 cDNA sequence, which shows a much higher degree of similarity both within transmembrane domains M1 –M3 and overall to the rat GABA receptor β subunit than to any other vertebrate GABA receptor subunit group. LCCH3 also exhibits a high degree of predicted amino acid sequence identity to β subunit-like cDNA fragment previously isolated from *Drosophila melanogaster* (Sattelle et al., 1991, *In Transmitter amino acid receptors: Structures, transduction and models for drug development* (Edited by E. A. Barnard and E. Costa) pp. 273–291, Thieme Medical Publishers, New York, which disclosure is hereby incorporated by reference). However, the lack of either a published nucleotide sequence or a cytogenetic location for that cDNA fragment precludes a determination of whether it and LCCH3 are identical.

The localization of LCCH3 to cytogenetic region 13F may provide additional insight into the function of the product of this gene. Region 13F also contains the slrp (slow receptor potential) locus, identified on the basis of mutants exhibiting altered electroretinogram potentials (Pak 1975) and behavioral deficits that include general hypoactivity, ether-induced leg shaking, and cold-induced paralysis (Homyk, T. Jr., 1977, *Genetics*, vol. 87, pp. 105–128; Homyk et al., 1977, *Genetics*, vol. 87, pp. 95–104; Homyk et al., 1989, *J. Neurogenet.*, vol. 5, pp. 37–48, which disclosures are hereby incorporated by reference). The various manifestations of the slrp phenotype, which involve or implicate abnormal transmission at neuronal or neuromuscular synapses (Homyk et al., 1989, cited elsewhere herein, which disclosure is hereby incorporated by reference), are consistent with the existence of a neurotransmitter receptor gene at this locus.

In Harvey et al., 1991, cited elsewhere herein, which disclosure is hereby incorporated by reference, the authors found that the positions of six intron-exon splice junctions in the *Lymnaea stagnalis* GABA receptor β subunit gene were conserved in position when compared to splice junctions in vertebrate GABA receptor β and δ subunits that have been characterized at the level of genomic organization. Moreover, this conservation did not extend to glycine receptor subunit genes or other, more distantly related members of the ligand-gated ion channel gene superfamily (Sommer et al., 1990, DNA Cell Biol., vol. 9, pp. 561–568; and Kirkness et al., 1991, Genomics, vol. 10, pp. 985–995, which disclosures are hereby incorporated by reference). These observations led the authors in Harvey et al., to conclude that the structural organization of GABA receptor genes was established prior to the evolutionary divergence of molluscs and chordates and prior to the duplication and divergence events that established the different GA3A receptor subtypes.

Figure 3:
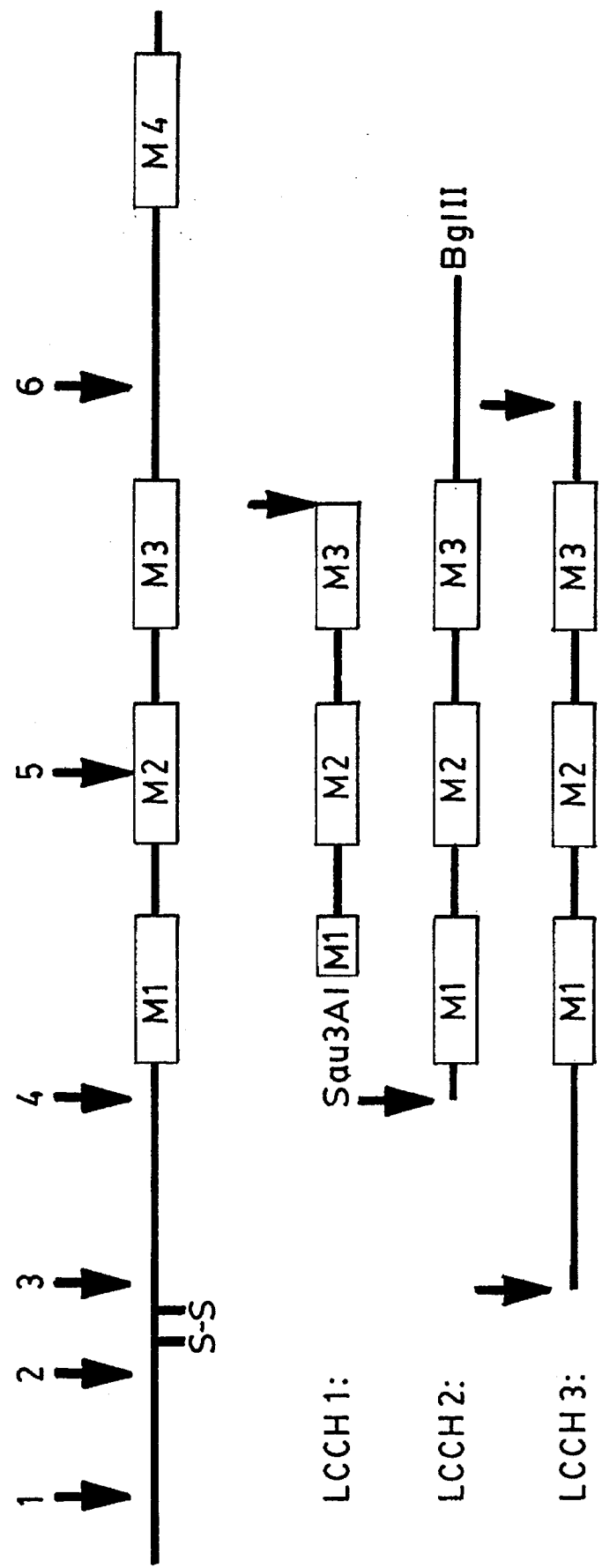
FIG. 3 is a schematic diagram illustrating positions of intron-exon splice junctions in Lymnaea and vertebrate GABA receptor subunit genes and in LCCH1, LCCH2 and LCCH3.

It was determined that each of the three *Drosophila melanogaster* sequences examined lacked at least one of the six conserved intron-exon splice junctions (Harvey et al., 1991, cited elsewhere herein, which disclosure is hereby incorporated by reference, and FIG. 3). Rdl (=LCCH1) lacked both the fourth (upstream of M1) and fifth (within M2) conserved splice junctions, and it also contained a nonconserved splice junction in M3 (ffrench-Constant et al., 1992, cited elsewhere herein, which disclosure is hereby incorporated by reference). LCCH2 lacked the fifth conserved splice junction in M2 and also contained uninterrupted coding sequence extending downstream well beyond the sixth conserved splice junction (within the M3–M4 intracellular loop). However, the splice junction at the N-terminus of the LCCH2 open reading frame was conserved in both position and amino acid sequence context. LCCH3 contained splice junctions at the termini of the open reading frame that appear to be conserved with respect to vertebrate and molluscan genes. The splice junction at the 5' end of the open reading frame was conserved both in position relative to M1 and amino acid sequence context. The splice junction at the 3' end of the LCCH3 open reading frame was approximately conserved in position relative to M3 but occurred in a region of low amino acid sequence conservation. On the basis of our results and those of others (ffrench-Constant et al., 1992, *Neurochem.*, vol. 59, pp. 1562–1565, which disclosure is hereby incorporated by reference), it is concluded that there is considerable but not absolute conservation of intron location among structurally-divergent members of the ligand-gated chloride channel gene family of *Drosophila melanogaster*.

The gene product of LCCH3 exhibited all of the conserved features commonly found in members of this gene family: a structural organization encompassing a large N-terminal extracellular domain, four hydrophobic domains capable of forming transmembrane helices, and a large intracellular domain lying between transmembrane domains M3 and M4; the conserved octapeptide (-TTVLTMTT) (SEQ.ID.NO.1) "signature motif" for this gene family located in M2; and the conserved cysteine residues and associated sequence elements capable of forming the disulfide-bridged loop structure in the extracellular domain (Burt et al., 1991, cited elsewhere herein; Langosch et al., 1990, *Eur. J. Biochem.*, vol. 194, pp. 1–8; and Barnard et al., 1987, cited elsewhere herein, which disclosures are hereby incorporated by reference).

Within the ligand-gated chloride channel gene family, LCCH3 is most similar to members of the GABA receptor β subunit sequence subfamily (Table 3).

TABLE 3[1,2,3,4]

|       | Lym β   | β1      | ρ1      | Glα     | Rdl     | γ2      | δ       | α1      |
|-------|---------|---------|---------|---------|---------|---------|---------|---------|
| LCCH3 | 98 (56) | 77 (47) | 69 (34) | 68 (31) | 64 (26) | 61 (28) | 59 (32) | 57 (29) |
| Lym β | —       | 77 (46) | 68 (35) | 68 (32) | 64 (26) | 59 (28) | 61 (33) | 56 (29) |
| β1    | —       | —       | 63 (35) | 66 (30) | 59 (28) | 61 (31) | 56 (38) | 51 (30) |
| ρ1    | —       | —       | —       | 59 (29) | 55 (23) | 54 (26) | 54 (31) | 49 (27) |
| Glα   | —       | —       | —       | —       | 62 (28) | 64 (30) | 56 (31) | 64 (30) |
| Rdl   | —       | —       | —       | —       | —       | 54 (26) | 57 (24) | 51 (22) |
| γ2    | —       | —       | —       | —       | —       | —       | 57 (31) | 67 (41) |
| δ     | —       | —       | —       | —       | —       | —       | —       | 50 (29) |

[1] Values expressed as percentages.
[2] α1, β1, γ2 and δ are bovine α1 and β1, and rat γ2 and δ GABA$_A$ receptor subunits, respectively. ρ1 is an unusual rat GABA receptor subunit that is prominently expressed in retina and possesses distinct pharmacological character consistent with its designation as a GABA$_C$ receptor subunit. Glα is the rat α1 glycine receptor subunit. Lym β is a GABA receptor β subunit from *Lymnaea stagnalis*. Rdl is a presumptive GABA receptor subunit of *D. melanogaster*, which was isolated from a genetic locus conferring resistance to chlorinated cyclodiene insecticides and is identical to the independently isolated LCCH1 sequence.
[3] Corresponds to amino acid residues 239 to 322 of the LCCH3 gene.
[4] Values in parentheses reflect optimal alignments of sequences obtained with the GCG solfware.

Over its entire coding region, LCCH3 exhibits 56% sequence identity with the *L. stagnalis* GABA receptor β subunit (Harvey et al., 1991, cited elsewhere herein, which disclosure is hereby incorporated by reference) and 47% identity with the bovine GABA receptor β1 subunit (Ymer et al., 1989, cited elsewhere herein, which disclosure is hereby incorporated by reference). Within the highly conserved core region of the gene product encompassing transmembrane domains M1 through M3, LCCH3 exhibits 98% amino acid identity with the *L. stagnalis* GABA receptor β subunit (Harvey et al., 1991, cited elsewhere herein, which disclosure is hereby incorporated by reference) and 77% identity with the bovine GABA receptor β1 subunit (Ymer et al., 1989, cited elsewhere herein, which disclosure is hereby incorporated by reference). The high sequence conservation between LCCH3 and the *L. stagnalis* GABA receptor β subunit in the M1–M3 core region strongly suggests from structural grounds that the isolated gene fragment of the present invention LCCH3 is the homologue in *D. melanogaster* of the *L. stagnalis* subunit (Zaman et al., 1992, *FEBS Lett.*, vol. 307, pp. 351–354, which disclosure is hereby incorporated by reference).

Despite the overall similarity of LCCH3 to other members of the GABA receptor β subunit sequence subfamily, it lacks the consensus sequence for a cAmp-dependent phosphorylation site that is found in the M3–M4 intracellular loop of all other known vertebrate and invertebrate β subunits (Burt et al., 1991, cited elsewhere herein; and Harvey et al., cited elsewhere herein, which disclosures are hereby incorporated by reference). Recent studies have shown that this site in the rat β1 subunit is a substrate for phosphorylation by both cAMP-dependent protein kinase and protein kinase C (Moss et al., 1992, *J. Biol. Chem.*, vol. 267, pp. 14470–14476, which disclosure is hereby incorporated by reference) and that phosphorylation by cAMP-dependent protein kinase modulates the responses to GABA of heteromultimeric (α1/β1 or α1/β1/γ2) receptors expressed in transfected cells Moss et al., 1992, *Science*, vol. 257, pp. 661–665, which disclosure is hereby incorporated by reference). The findings of the present invention nevertheless identify two possible phosphorylation sites with alternative recognition cAMP-dependent protein kinase. Alternatively, these receptors in *Drosophila melanogaster* might be modulated by phosphorylation on other, as yet unidentified subunits or by mechanisms other than cAMP-dependent phosphorylation.

The LCCH3 gene product is less similar to the other known GABA receptor-like sequence from *Drosophila melanogaster*, the Rdl gene product (ffrench-Constant et al., 1991, cited elsewhere herein, which disclosure is hereby incorporated by reference), than to members of the β subunit sequence subfamily (FIG. 6 and Table 3). The inferred amino acid sequence of LCCH3 possesses only 26% identity overall to Rdl, and the degree of identity in the M1–M3 core region is only 64%. The existence in *Drosophila melanogaster* of two divergent members of this sequence family raises the possibility that the two gene products could form subunits of a heteromultimeric receptor. Based on the properties of the homomultimeric and chimeric receptors formed by the *L. stagnalis* subunit in Xenopus oocytes (Harvey et al., 1991, and Zaman et al., 1992, *FEBS Lett.*, vol. 307, pp. 351–354, cited elsewhere herein, which disclosures are hereby incorporated by reference), it is likely that the LCCH3 gene product would need to be co-expressed with another subunit to form a receptor that exhibits the pharmacological properties of GABA receptors in insect tissues. The linkage between the Rdl gene product and GABA receptor function is based on the ability of a mutation at the Rdl locus to confer resistance to picrotoxinin and cyclodiene insecticides, which act as blockers of the GABA-gated chloride channel (ffrench-Constant et al., 1991, cited elsewhere herein, Bloomquist et al., 1991, *Pestic. Sci.*, vol. 32, pp. 463–469, which disclosures are hereby incorporated by reference).

Although the invention has been described in detail for the purpose of illustration, it is understood that such detail is solely for that purpose, and variations can be made therein by those skilled in the art without departing from the spirit and scope of the invention which is described by the following claims.

What is claimed is:

1. An isolated DNA molecule which encodes a γ-aminobutyric acid receptor subunit having the amino acid sequence shown in SEQ ID NO: 2.

2. An isolated DNA molecule encoding a γ-aminobutyric acid receptor subunit, said DNA molecule having the nucleotide sequence shown in SEQ ID NO: 3.

3. A recombinant DNA vector comprising the DNA molecule according to claim 2.

4. The vector of claim 3 wherein said vector is selected from the group consisting of a plasmid, a virus, and a bacteriophage.

5. A cell transformed with the recombinant DNA vector according to claim 3.

6. A method of expressing an invertebrate γ-aminobutyric acid receptor, comprising:

transforming a host cell with the DNA molecule encoding an γ-aminobutyric acid receptor subunit according to claim 2 and at least one other DNA molecule encoding another γ-aminobutyric acid receptor subunit; and facilitating co-expression of said γ-aminobutyric acid receptor subunit encoded by said DNA molecule and said another γ-aminobutyric acid receptor subunit encoded by said other DNA molecule in the host cell, wherein said co-expression results in the formation and expression of an γ-aminobutyric acid receptor.

7. The method according to claim 6, wherein said another γ-aminobutyric acid receptor subunit is selected from the group consisting of the rat γ-aminobutyric acid$_A$ receptor α subunit and a γ-aminobutyric acid$_A$ receptor γ subunit.

8. A method of screening a chemical agent for effectiveness as a pesticide, comprising:

transforming a host cell with the DNA molecule encoding an γ-aminobutyric acid receptor subunit according to claim 2 and at least one other DNA molecule encoding another γ-aminobutyric acid receptor subunit;

facilitating co-expression of said γ-aminobutyric acid receptor subunit encoded by said DNA molecule and said another γ-aminobutyric acid receptor subunit encoded by said other DNA molecule in the host cell, wherein said co-expression results in the formation and expression of an γ-aminobutyric acid receptor in the cell;

exposing the cell to a chemical agent; and evaluating the exposed cell to determine if the receptor is the target site for the chemical agent, wherein if said receptor is the target site for said chemical agent, said chemical agent is effective as a pesticide.

* * * * *

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Thr  Thr  Val  Leu  Thr  Met  Thr  Thr
1                  5
```

( 2 ) INFORMATION FOR SEQ ID NO:2:

( i ) SEQUENCE CHARACTERISTICS:
        ( A ) LENGTH: 496 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Thr  Cys  Phe  Thr  Arg  Val  Gly  Val  Ser  Cys  Ser  Leu  Phe  Phe  Phe
1                  5                 10                            15

Leu  Leu  Gly  Ala  Gln  Leu  Gln  Leu  Ile  Arg  Cys  Ile  Arg  Lys  Asp  Val
                20                 25                           30

Leu  Ala  Gly  Arg  Leu  Glu  Asn  Val  Thr  Gln  Thr  Ile  Ser  Asn  Ile  Leu
           35                 40                       45

Gln  Gly  Tyr  Asp  Ile  Arg  Leu  Arg  Pro  Asn  Phe  Gly  Gly  Glu  Pro  Leu
     50                      55                      60

His  Val  Gly  Met  Asp  Leu  Thr  Ile  Ala  Ser  Phe  Asp  Ala  Ile  Ser  Glu
65                       70                      75                        80

Val  Asn  Met  Asp  Tyr  Thr  Ile  Thr  Met  Tyr  Leu  Asn  Gln  Tyr  Trp  Arg
                85                      90                      95

Asp  Glu  Arg  Leu  Ala  Phe  Asn  Ile  Phe  Gly  Gln  Tyr  Phe  Asp  Asp  Glu
               100                    105                     110

Asn  Asp  Asp  Gly  Ile  Ser  Asp  Val  Leu  Thr  Leu  Ser  Gly  Asp  Phe  Ala
          115                      120                    125

Glu  Lys  Ile  Trp  Val  Pro  Asp  Thr  Phe  Phe  Ala  Asn  Asp  Lys  Asn  Ser
     130                     135                    140

Phe  Leu  His  Asp  Val  Thr  Glu  Arg  Asn  Lys  Leu  Val  Arg  Leu  Gly  Gly
145                     150                    155                       160

Asp  Gly  Ala  Val  Thr  Tyr  Gly  Met  Arg  Phe  Thr  Thr  Thr  Leu  Ala  Cys
                165                    170                       175

Met  Met  Asp  Leu  His  Tyr  Tyr  Pro  Leu  Asp  Ser  Gln  Asn  Cys  Thr  Val
               180                    185                     190

Glu  Ile  Glu  Ser  Tyr  Gly  Tyr  Thr  Val  Ser  Asp  Val  Val  Met  Tyr  Trp
          195                     200                    205

Lys  Pro  Thr  Pro  Val  Arg  Gly  Val  Glu  Asp  Ala  Glu  Leu  Pro  Gln  Phe
     210                     215                    220

Thr  Ile  Ile  Gly  Tyr  Glu  Thr  Asn  Asp  Arg  Lys  Glu  Arg  Leu  Ala  Thr
225                     230                    235                       240

Gly  Val  Tyr  Gln  Arg  Leu  Ser  Leu  Ser  Phe  Lys  Leu  Gln  Arg  Asn  Ile
```

|     |     |     |     |     |     |     |     |     |     |     |     |     |     |     |
| --- | --- | --- | --- | --- | --- | --- | --- | --- | --- | --- | --- | --- | --- | --- |
|     |     |     | 245 |     |     |     | 250 |     |     |     |     | 255 |     |     |
| Gly | Tyr | Phe | Val | Phe | Gln | Thr | Tyr | Leu | Pro | Ser | Ile | Leu | Ile | Val | Met |
|     |     |     | 260 |     |     |     | 265 |     |     |     |     | 270 |     |     |
| Leu | Ser | Trp | Val | Ser | Phe | Trp | Ile | Asn | His | Glu | Ala | Thr | Ser | Ala | Arg |
|     |     | 275 |     |     |     | 280 |     |     |     |     | 285 |     |     |     |
| Val | Ala | Leu | Gly | Ile | Thr | Thr | Val | Leu | Thr | Met | Thr | Thr | Ile | Ser | Thr |
|     | 290 |     |     |     |     | 295 |     |     |     |     | 300 |     |     |     |     |
| Gly | Val | Arg | Ser | Ser | Leu | Pro | Arg | Ile | Ser | Tyr | Val | Lys | Ala | Ile | Asp |
| 305 |     |     |     |     | 310 |     |     |     |     | 315 |     |     |     |     | 320 |
| Ile | Tyr | Leu | Val | Met | Cys | Phe | Val | Phe | Val | Phe | Ala | Ala | Leu | Leu | Glu |
|     |     |     |     | 325 |     |     |     |     | 330 |     |     |     |     | 335 |     |
| Tyr | Ala | Ala | Val | Asn | Tyr | Thr | Tyr | Trp | Gly | Lys | Arg | Ala | Lys | Lys | Lys |
|     |     |     | 340 |     |     |     |     | 345 |     |     |     |     | 350 |     |     |
| Ile | Lys | Lys | Val | Lys | Glu | Cys | Cys | Pro | Gly | Lys | Ile | Gly | Lys | Ser | Glu |
|     |     | 355 |     |     |     |     | 360 |     |     |     |     | 365 |     |     |     |
| Arg | Ser | Glu | Thr | Cys | Ser | Thr | Thr | Glu | Asp | Ile | Ile | Glu | Leu | Gln | Asp |
|     | 370 |     |     |     |     |     | 375 |     |     |     |     | 380 |     |     |     |
| Val | Arg | Met | Ser | Pro | Ile | Pro | Ser | Leu | Arg | Arg | Gly | Thr | Tyr | Asn | Ala |
| 385 |     |     |     |     | 390 |     |     |     |     | 395 |     |     |     |     | 400 |
| Thr | Leu | Asp | Ser | Ile | Gly | Thr | Glu | Thr | Met | Asn | Leu | Gly | Lys | Phe | Pro |
|     |     |     |     | 405 |     |     |     |     | 410 |     |     |     |     | 415 |     |
| Pro | Ser | Phe | Arg | Ile | Thr | Arg | Asn | Tyr | Gly | Thr | Gly | His | Ser | Gln | Leu |
|     |     |     | 420 |     |     |     |     | 425 |     |     |     |     | 430 |     |     |
| Arg | Arg | Arg | Ala | Gln | Arg | Gly | Ile | Ser | Thr | Arg | Pro | Arg | Met | Leu | His |
|     |     | 435 |     |     |     |     | 440 |     |     |     |     | 445 |     |     |     |
| Ala | Leu | Lys | Arg | Gly | Ala | Ser | Ala | Ile | Lys | Ala | Thr | Ile | Pro | Lys | Ile |
|     | 450 |     |     |     |     | 455 |     |     |     |     | 460 |     |     |     |     |
| Lys | Asp | Val | Asn | Ile | Ile | Asp | Lys | Tyr | Ser | Arg | Met | Ile | Phe | Pro | Ile |
| 465 |     |     |     |     | 470 |     |     |     |     | 475 |     |     |     |     | 480 |
| Ser | Phe | Leu | Ala | Phe | Asn | Leu | Gly | Tyr | Trp | Leu | Phe | Tyr | Ile | Leu | Glu |
|     |     |     |     | 485 |     |     |     |     | 490 |     |     |     |     | 495 |     |

( 2 ) INFORMATION FOR SEQ ID NO:3:

( i ) SEQUENCE CHARACTERISTICS:
        ( A ) LENGTH: 1491 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
ATGACATGTT TTACGCGCGT CGGAGTATCC TGTAGCCTGT TCTTTTTCCT ACTGGGCGCC      60
CAGCTACAAT TGATTCGATG CATTCGAAAG GATGTACTAG CTGGCCGCCT TGAGAACGTG     120
ACGCAAACAA TATCAAACAT ACTGCAAGGA TACGATATTC GACTTAGGCC CAATTTCGGA     180
GGAGAGCCAC TACATGTCGG CATGGATTTG ACCATCGCCA GCTTTGATGC CATATCAGAA     240
GTTAACATGG ATTATACGAT AACAATGTAT TTAAATCAGT ATTGGCGCGA CGAGCGTTTG     300
GCATTTAATA TCTTTGGACA ATATTTCGAC GATGAGAATG ATGATGGCAT AAGCGATGTG     360
CTGACATTAT CCGGAGACTT TGCTGAAAAG ATATGGGTAC CGGATACGTT CTTCGCCAAT     420
GACAAAAACA GTTTTCTGCA CGATGTCACC GAAAGGAACA AACTGGTGCG ACTTGGCGGC     480
GATGGAGCTG TTACTTATGG CATGAGATTC ACCACGACCC TCGCCTGCAT GATGGATCTG     540
CACTACTATC CATTGGACTC GCAGAATTGC ACTGTGGAAA TTGAGAGCTA TGGATACACG     600
```

```
GTCAGCGATG TGGTCATGTA CTGGAAGCCA ACGCCAGTGC GCGGAGTGGA GGATGCGGAG    660

CTGCCGCAGT TCACCATCAT TGGGTATGAG ACCAATGACC GAAAGGAGCG GCTGGCCACT    720

GGAGTCTATC AGCGCCTCTC GCTCTCATTC AAACTGCAAC GGAATATCGG ATACTTTGTA    780

TTCCAAACTT ATCTGCCCAG CATTCTGATC GTAATGCTGT CGTGGGTCTC GTTCTGGATT    840

AACCACGAGG CGACGAGTGC CCGGGTTGCA TTGGGCATCA CCACGGTGCT CACCATGACC    900

ACCATTAGCA CGGGTGTTCG CAGCTCACTG CCGCGCATAT CGTATGTGAA GGCGATCGAC    960

ATTTATCTGG TCATGTGCTT CGTTTTCGTG TTCGCAGCCC TCTTGGAATA CGCTGCCGTT   1020

AACTATACTT ACTGGGGCAA AAGGGCTAAA AAGAAAATAA AGAAAGTCAA AGAATGTTGT   1080

CCAGGCAAGA TCGGAAAGAG TGAAAGATCC GAGACGTGTT CAACGACAGA GGACATTATC   1140

GAGCTGCAGG ATGTTCGAAT GAGTCCTATA CCATCTTTGC GAAGAGGTAC CTACAATGCC   1200

ACCCTCGACT CCATCGGCAC CGAGACCATG AATCTAGGAA AGTTCCCCCC AAGTTTTCGA   1260

ATAACTCGTA ATTATGGCAC CGGACATAGC CAGCTTAGAC GTCGCGCCCA AAGGGGTATC   1320

TCAACCCGCC CACGCATGTT GCACGCCCTG AAGAGAGGTG CCTCTGCTAT TAAGGCAACC   1380

ATACCGAAGA TCAAAGATGT CAATATTATT GACAAATACT CCCGAATGAT ATTTCCGATC   1440

AGTTTTCTTG CGTTCAATCT TGGCTACTGG CTGTTTTATA TTCTGGAATG A           1491
```

(2) INFORMATION FOR SEQ ID NO:4:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
GATCCTGTGA T                                                          11
```

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
AAGTCACGTC ATGAGTCCGA CAG                                             23
```

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
AAGTCACGTC ATGAGTCC                                                   18
```

(2) INFORMATION FOR SEQ ID NO:7:

(i) SEQUENCE CHARACTERISTICS:
        (A) LENGTH: 42 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:7:

GTAAAAGGAC GGCCAGTCTA GAACNACNGT NYTGACNATG AC          42

(2) INFORMATION FOR SEQ ID NO:8:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:8:

TGAAAAGGAC GGCCAGTCTA GAACNACNGT NCTYACNATG AC          42

(2) INFORMATION FOR SEQ ID NO:9:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:9:

GTAAAAGGAC GGCCAGTCTA GAACNACNGT NYTAACNATG AC          42

(2) INFORMATION FOR SEQ ID NO:10:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:10:

GGGAATTCRA ANACRAANAC RAARCA                             26

(2) INFORMATION FOR SEQ ID NO:11:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:11:

GCCGCAGTTC ACCATCATTG                                    20

(2) INFORMATION FOR SEQ ID NO:12:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA ( x i ) SEQUENCE DESCRIPTION: SEQ ID NO:12:

AGTGAGCTGC GAACACCCGT G                                                                21

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

TTTCGTGTTC GCAGCCTCT                                                                   20

( 2 ) INFORMATION FOR SEQ ID NO:14:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

GGTCTAGAAG TCAATCTTTA TTATGGAGG                                                        29

( 2 ) INFORMATION FOR SEQ ID NO:15:

( i ) SEQUENCE CHARACTERISTICS:
        ( A ) LENGTH: 52 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

```
Ala Thr Pro Ala Arg Val Ala Leu Gly Val Thr Thr Val Leu Thr Met
1               5                   10                  15
Thr Thr Leu Met Ser Ser Thr Asn Ala Ala Leu Pro Lys Ile Ser Tyr
            20                  25                  30
Val Lys Ser Ile Asp Val Tyr Leu Gly Thr Cys Phe Val Met Val Phe
        35                  40                  45
Ala Ser Leu Leu
        50
```

( 2 ) INFORMATION FOR SEQ ID NO:16:

( i ) SEQUENCE CHARACTERISTICS:
        ( A ) LENGTH: 57 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

```
Ala Thr Ala Asp Arg Val Ser Leu Gly Ile Thr Thr Val Leu Thr Met
1               5                   10                  15
Thr Phe Leu Gly Leu Glu Ala Arg Thr Asp Leu Pro Lys Val Ser Tyr
            20                  25                  30
Pro Thr Ala Leu Asp Phe Phe Val Phe Leu Ser Phe Gly Phe Ile Phe
        35                  40                  45
```

```
Ala  Thr  Ile  Leu  Gln  Phe  Ala  Val  Val
     50                  55
```

( 2 ) INFORMATION FOR SEQ ID NO:17:

( i ) SEQUENCE CHARACTERISTICS:
        ( A ) LENGTH: 57 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

```
Ala  Thr  Ser  Ala  Arg  Val  Ala  Leu  Gly  Ile  Thr  Thr  Val  Leu  Thr  Met
1              5                        10                       15
Thr  Thr  Ile  Ser  Thr  Gly  Val  Arg  Ser  Ser  Leu  Pro  Arg  Ile  Ser  Tyr
               20                       25                       30
Val  Lys  Ala  Ile  Asp  Ile  Tyr  Leu  Cys  Met  Cys  Phe  Val  Phe  Val  Phe
               35                       40                       45
Ala  Ala  Leu  Leu  Glu  Tyr  Ala  Ala  Val
     50                  55
```

( 2 ) INFORMATION FOR SEQ ID NO:18:

( i ) SEQUENCE CHARACTERISTICS:
        ( A ) LENGTH: 57 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

```
Ala  Thr  Ser  Ala  Arg  Val  Ala  Leu  Gly  Ile  Thr  Thr  Val  Leu  Thr  Met
1              5                        10                       15
Thr  Thr  Ile  Ser  Asn  Gly  Val  Arg  Ser  Ser  Leu  Pro  Arg  Ile  Ser  Tyr
               20                       25                       30
Val  Lys  Ala  Ile  Asp  Ile  Tyr  Leu  Val  Met  Cys  Phe  Val  Phe  Val  Phe
               35                       40                       45
Ala  Ala  Leu  Leu  Glu  Tyr  Ala  Ala  Val
     50                  55
```

( 2 ) INFORMATION FOR SEQ ID NO:19:

( i ) SEQUENCE CHARACTERISTICS:
        ( A ) LENGTH: 57 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

```
Ser  Val  Pro  Ala  Arg  Thr  Val  Phe  Gly  Val  Thr  Thr  Val  Leu  Thr  Met
1              5                        10                       15
Thr  Thr  Leu  Ser  Ile  Ser  Ala  Arg  Asn  Ser  Leu  Pro  Lys  Val  Ala  Tyr
               20                       25                       30
Ala  Thr  Ala  Met  Asp  Trp  Phe  Ile  Ala  Val  Cys  Tyr  Ala  Phe  Val  Phe
               35                       40                       45
Ser  Ala  Leu  Ile  Glu  Phe  Ala  Thr  Val
     50                  55
```

( 2 ) INFORMATION FOR SEQ ID NO:20:

( i ) SEQUENCE CHARACTERISTICS:
        ( A ) LENGTH: 57 amino acids (B) TYPE: amino acid
(D) TOPOLOGY: linear (i i) MOLECULE TYPE: peptide (x i) SEQUENCE DESCRIPTION: SEQ ID NO:20:

| Ala | Ser | Ala | Ala | Arg | Val | Ala | Leu | Gly | Ile | Thr | Thr | Val | Leu | Thr | Met |
|---|---|---|---|---|---|---|---|---|---|---|---|---|---|---|---|
| 1 | | | | 5 | | | | | 10 | | | | | 15 | |

| Thr | Thr | Ile | Ser | Thr | His | Leu | Arg | Glu | Thr | Leu | Pro | Lys | Ile | Pro | Tyr |
|---|---|---|---|---|---|---|---|---|---|---|---|---|---|---|---|
| | | | 20 | | | | | 25 | | | | | 30 | | |

| Val | Lys | Ala | Ile | Asp | Ile | Tyr | Leu | Met | Gly | Cys | Phe | Val | Phe | Val | Phe |
|---|---|---|---|---|---|---|---|---|---|---|---|---|---|---|---|
| | | 35 | | | | | 40 | | | | | 45 | | | |

| Leu | Ala | Leu | Leu | Glu | Tyr | Ala | Phe | Val |
|---|---|---|---|---|---|---|---|---|
| 50 | | | | | 55 | | | |

(2) INFORMATION FOR SEQ ID NO:21:

(i) SEQUENCE CHARACTERISTICS:
(A) LENGTH: 57 amino acids
(B) TYPE: amino acid
(D) TOPOLOGY: linear (i i) MOLECULE TYPE: peptide (x i) SEQUENCE DESCRIPTION: SEQ ID NO:21:

| Ala | Val | Pro | Ala | Arg | Thr | Ser | Leu | Gly | Ile | Thr | Thr | Val | Leu | Thr | Met |
|---|---|---|---|---|---|---|---|---|---|---|---|---|---|---|---|
| 1 | | | | 5 | | | | | 10 | | | | | 15 | |

| Thr | Thr | Leu | Ser | Thr | Ile | Ala | Arg | Lys | Ser | Leu | Pro | Lys | Val | Ser | Tyr |
|---|---|---|---|---|---|---|---|---|---|---|---|---|---|---|---|
| | | | 20 | | | | | 25 | | | | | 30 | | |

| Val | Thr | Ala | Met | Asp | Leu | Phe | Val | Ser | Val | Cys | Phe | Ile | Phe | Val | Phe |
|---|---|---|---|---|---|---|---|---|---|---|---|---|---|---|---|
| | | 35 | | | | | 40 | | | | | 45 | | | |

| Ser | Ala | Leu | Val | Glu | Tyr | Gly | Thr | Leu |
|---|---|---|---|---|---|---|---|---|
| 50 | | | | | 55 | | | |

(2) INFORMATION FOR SEQ ID NO:22:

(i) SEQUENCE CHARACTERISTICS:
(A) LENGTH: 57 amino acids
(B) TYPE: amino acid
(D) TOPOLOGY: linear (i i) MOLECULE TYPE: peptide (x i) SEQUENCE DESCRIPTION: SEQ ID NO:22:

| Ala | Val | Pro | Ala | Arg | Val | Ser | Leu | Gly | Ile | Thr | Thr | Val | Leu | Thr | Met |
|---|---|---|---|---|---|---|---|---|---|---|---|---|---|---|---|
| 1 | | | | 5 | | | | | 10 | | | | | 15 | |

| Thr | Thr | Leu | Met | Val | Ser | Ala | Arg | Ser | Ser | Leu | Pro | Arg | Ala | Ser | Ala |
|---|---|---|---|---|---|---|---|---|---|---|---|---|---|---|---|
| | | | 20 | | | | | 25 | | | | | 30 | | |

| Ile | Lys | Ala | Leu | Asp | Val | Tyr | Phe | Trp | Ile | Cys | Tyr | Val | Phe | Val | Phe |
|---|---|---|---|---|---|---|---|---|---|---|---|---|---|---|---|
| | | 35 | | | | | 40 | | | | | 45 | | | |

| Ala | Ala | Leu | Val | Glu | Tyr | Ala | Phe | Ala |
|---|---|---|---|---|---|---|---|---|
| 50 | | | | | 55 | | | |

(2) INFORMATION FOR SEQ ID NO:23:

(i) SEQUENCE CHARACTERISTICS:
(A) LENGTH: 57 amino acids
(B) TYPE: amino acid
(D) TOPOLOGY: linear (i i) MOLECULE TYPE: peptide (x i) SEQUENCE DESCRIPTION: SEQ ID NO:23:

| Ala | Ala | Pro | Ala | Arg | Val | Gly | Leu | Gly | Ile | Thr | Thr | Val | Leu | Thr | Met |
|---|---|---|---|---|---|---|---|---|---|---|---|---|---|---|---|

```
  1                   5                        10                       15
Thr  Thr  Gln  Ser  Ser  Gly  Ser  Arg  Ala  Ser  Leu  Pro  Lys  Val  Ser  Tyr
               20                   25                   30

Val  Lys  Ala  Ile  Asp  Ile  Trp  Met  Ala  Val  Cys  Leu  Leu  Phe  Val  Phe
               35                   40                   45

Ser  Ala  Leu  Leu  Glu  Tyr  Ala  Ala  Val
          50                   55
```

( 2 ) INFORMATION FOR SEQ ID NO:24:

( i ) SEQUENCE CHARACTERISTICS:
        ( A ) LENGTH: 617 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

```
Xaa  Xaa  Xaa  Xaa  Xaa  Xaa  Xaa  Xaa  Xaa  Xaa  Met  Trp  Gly  Ile  Ile  Val
1                   5                        10                       15

Pro  Xaa  Phe  Phe  Ser  Ala  Ser  Leu  Met  Cys  Ser  Leu  Val  Ala  Val  Xaa
               20                   25                   30

Xaa  Xaa  Xaa  Xaa  Xaa  Xaa  Xaa  Xaa  Val  Arg  Cys  Gln  Gln  Asp  Xaa  Xaa
               35                   40                   45

Xaa  Thr  Asp  His  Phe  Xaa  Xaa  Xaa  Ala  Asn  Val  Thr  Asn  Thr  Ile  Asp
     50                   55                        60

Ser  Leu  Leu  Lys  Gly  Tyr  Asp  Ile  Arg  Leu  Arg  Pro  Ser  Phe  Gly  Gly
65                   70                   75                            80

Ala  Pro  Leu  Glu  Ile  Gly  Ile  Glu  Val  Ile  Leu  Ala  Ser  Phe  Asp  Ser
               85                   90                   95

Ile  Ser  Glu  Val  Asp  Met  Asp  Tyr  Thr  Ile  Thr  Met  Tyr  Leu  Asn  Gln
               100                  105                  110

Tyr  Trp  Arg  Asp  Glu  Arg  Leu  Gln  Phe  Xaa  Ile  Phe  Asn  Glu  Ser  Leu
               115                  120                  125

Asp  Leu  Gly  Glu  Asn  Arg  Ser  Val  Thr  Xaa  Thr  Met  Thr  Leu  Thr  Gly
     130                  135                  140

Ala  Phe  Ala  Glu  Lys  Ile  Trp  Val  Pro  Asp  Thr  Phe  Leu  Ala  Asn  Asp
145                       150                  155                       160

Lys  Asn  Ser  Phe  Leu  His  Asp  Ile  Thr  Glu  Lys  Asn  Lys  Met  Val  Arg
               165                  170                  175

Leu  Tyr  Gly  Asn  Gly  Ser  Leu  Val  Tyr  Gly  Met  Arg  Phe  Thr  Thr  Thr
               180                  185                  190

Leu  Ala  Cys  Met  Met  Asp  Leu  His  Asn  Tyr  Pro  Leu  Asp  His  Gln  Glu
               195                  200                  205

Cys  Thr  Val  Glu  Ile  Glu  Ser  Tyr  Gly  Tyr  Thr  Met  Asp  Asp  Ile  Val
     210                       215                  220

Leu  Tyr  Trp  Leu  Asn  Asp  Arg  Gly  Ala  Val  Thr  Gly  Val  Glu  Asp  Val
225                       230                  235                       240

Ser  Leu  Pro  Gln  Phe  Ser  Ile  Thr  Asn  Tyr  Ala  Thr  Ile  Asn  Lys  Ile
               245                  250                       255

Glu  Glu  Leu  Ser  Thr  Gly  Asp  Tyr  Gln  Arg  Leu  Ser  Leu  Ile  Phe  Gln
               260                  265                  270

Leu  Gln  Arg  Asn  Ile  Gly  Tyr  Phe  Ile  Phe  Gln  Thr  Tyr  Leu  Pro  Ser
          275                  280                  285

Ile  Leu  Ile  Val  Met  Leu  Ser  Trp  Val  Ser  Phe  Trp  Ile  Asn  His  Glu
     290                       295                  300
```

```
Ala  Thr  Ser  Ala  Arg  Val  Ala  Leu  Gly  Ile  Thr  Thr  Val  Leu  Thr  Met
305                      310                      315                      320

Thr  Thr  Ile  Ser  Asn  Gly  Val  Arg  Ser  Ser  Leu  Pro  Arg  Ile  Ser  Tyr
                         325                      330                      335

Val  Lys  Ala  Ile  Asp  Ile  Tyr  Leu  Val  Met  Cys  Phe  Val  Phe  Val  Phe
                    340                      345                      350

Ala  Ala  Leu  Leu  Glu  Tyr  Ala  Ala  Val  Asn  Tyr  Thr  Tyr  Trp  Gly  Ala
               355                      360                      365

Arg  Ala  Lys  Arg  Lys  Ala  Lys  Arg  Leu  Arg  Glu  Arg  Ala  Thr  Ser  Val
          370                      375                      380

Arg  Lys  Arg  Val  Asp  Xaa  Xaa  Xaa  Xaa  Asp  Gly  Asp  Gln  Met  Asn  Asn
385                      390                      395                      400

Thr  Asn  Met  Asp  Thr  Val  Glu  Leu  Lys  Glu  Val  His  Met  Val  Pro  Thr
                    405                      410                      415

Ser  Val  Gly  Val  Thr  Asn  Ser  Gln  Ser  Phe  Xaa  Xaa  Xaa  Xaa  Xaa  Xaa
               420                      425                      430

Xaa  Xaa  Xaa  Xaa  Xaa  Xaa  Xaa  Xaa  Xaa  Xaa  Xaa  Xaa  Xaa  Xaa  Xaa  Xaa
               435                      440                      445

Xaa  Xaa  Xaa  Asn  Leu  Asp  Leu  Asp  Asp  Gly  Ser  Gly  Asp  Asp  Thr  Gly
     450                      455                      460

Phe  Arg  Val  Val  Pro  Xaa  Xaa  Xaa  Xaa  Xaa  Xaa  Xaa  Xaa  Xaa  Xaa  Xaa
465                      470                      475                      480

Xaa  Xaa  Xaa  Xaa  Xaa  Xaa  Xaa  Xaa  Xaa  Xaa  Xaa  Xaa  Xaa  Xaa  Xaa  Xaa
                    485                      490                      495

Xaa  Xaa  Xaa  Xaa  Xaa  Xaa  Xaa  Xaa  Xaa  Xaa  Xaa  Xaa  Xaa  Xaa  Xaa  Xaa
               500                      505                      510

Xaa  Pro  Ile  Pro  Arg  Ser  Phe  Thr  His  Ser  His  Ala  Thr  Thr  His  Gly
          515                      520                      525

Tyr  Ile  Pro  Thr  Asn  Val  Val  Arg  Arg  Arg  Ser  Ser  Ser  His  Val  Pro
     530                      535                      540

Pro  Arg  Arg  Arg  Arg  Leu  Leu  Ser  His  Phe  Arg  Gln  Lys  Ala  Lys  Ser
545                      550                      555                      560

Ile  Lys  Val  Lys  Ile  Pro  Arg  Val  Gln  Asp  Val  Xaa  Xaa  Asn  Thr  Ile
                    565                      570                      575

Asp  Lys  Tyr  Ala  Arg  Leu  Met  Phe  Pro  Leu  Leu  Phe  Ile  Ile  Phe  Asn
               580                      585                      590

Thr  Ser  Tyr  Trp  Ser  Val  Tyr  Leu  Leu  Thr  Xaa  Xaa  Xaa  Xaa  Xaa  Xaa
          595                      600                      605

Xaa  Xaa  Xaa  Xaa  Xaa  Xaa  Xaa  Xaa  Xaa
          610                      615
```

( 2 ) INFORMATION FOR SEQ ID NO:25:

( i ) SEQUENCE CHARACTERISTICS:
        ( A ) LENGTH: 617 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

```
Xaa  Xaa  Xaa  Xaa  Xaa  Xaa  Xaa  Xaa  Xaa  Xaa  Met  Trp  Thr  Val  Gln  Asn
1                   5                        10                       15

Arg  Glu  Ser  Leu  Gly  Leu  Leu  Ser  Phe  Pro  Val  Met  Val  Ala  Met  Xaa
                    20                       25                       30

Xaa  Xaa  Xaa  Xaa  Xaa  Xaa  Xaa  Xaa  Val  Cys  Cys  Ala  His  Ser  Ser  Asn
               35                       40                       45
```

| Glu | Pro | Ser | Asn | Met | Xaa | Xaa | Xaa | Ser | Tyr | Val | Lys | Glu | Thr | Val | Asp |
|---|---|---|---|---|---|---|---|---|---|---|---|---|---|---|---|
| | 50 | | | | 55 | | | | | 60 | | | | | |

| Arg | Leu | Leu | Lys | Gly | Tyr | Asp | Ile | Arg | Leu | Arg | Pro | Asp | Phe | Gly | Gly |
|---|---|---|---|---|---|---|---|---|---|---|---|---|---|---|---|
| 65 | | | | | 70 | | | | 75 | | | | | | 80 |

| Pro | Pro | Val | Asp | Val | Gly | Met | Arg | Ile | Asp | Val | Ala | Ser | Ile | Asp | Met |
|---|---|---|---|---|---|---|---|---|---|---|---|---|---|---|---|
| | | | | 85 | | | | | 90 | | | | | 95 | |

| Val | Ser | Glu | Val | Asn | Met | Asp | Tyr | Thr | Leu | Thr | Met | Tyr | Phe | Gln | Gln |
|---|---|---|---|---|---|---|---|---|---|---|---|---|---|---|---|
| | | | | 100 | | | | | 105 | | | | | 110 | |

| Ser | Trp | Lys | Asp | Lys | Arg | Leu | Ser | Tyr | Xaa | Xaa | Xaa | Xaa | Xaa | Xaa | Xaa |
|---|---|---|---|---|---|---|---|---|---|---|---|---|---|---|---|
| | | 115 | | | | | 120 | | | | | 125 | | | |

| Xaa | Xaa | Xaa | Xaa | Xaa | Ser | Gly | Ile | Pro | Leu | Asn | Leu | Thr | Leu | Asp | Asn |
|---|---|---|---|---|---|---|---|---|---|---|---|---|---|---|---|
| | 130 | | | | | 135 | | | | 140 | | | | | |

| Arg | Val | Ala | Asp | Gln | Leu | Trp | Val | Pro | Asp | Thr | Tyr | Phe | Leu | Asn | Asp |
|---|---|---|---|---|---|---|---|---|---|---|---|---|---|---|---|
| 145 | | | | | 150 | | | | | 155 | | | | | 160 |

| Lys | Lys | Ser | Phe | Val | His | Gly | Val | Thr | Val | Lys | Asn | Arg | Met | Ile | Arg |
|---|---|---|---|---|---|---|---|---|---|---|---|---|---|---|---|
| | | | | 165 | | | | | 170 | | | | | 175 | |

| Leu | His | Pro | Asp | Gly | Thr | Val | Leu | Tyr | Gly | Leu | Arg | Ile | Thr | Thr | Thr |
|---|---|---|---|---|---|---|---|---|---|---|---|---|---|---|---|
| | | | 180 | | | | | 185 | | | | | 190 | | |

| Ala | Ala | Cys | Met | Met | Asp | Leu | Arg | Arg | Tyr | Pro | Leu | Asp | Glu | Gln | Asn |
|---|---|---|---|---|---|---|---|---|---|---|---|---|---|---|---|
| | | 195 | | | | | 200 | | | | | 205 | | | |

| Cys | Thr | Leu | Glu | Ile | Glu | Ser | Tyr | Gly | Tyr | Thr | Thr | Asp | Asp | Ile | Glu |
|---|---|---|---|---|---|---|---|---|---|---|---|---|---|---|---|
| | 210 | | | | | 215 | | | | | 220 | | | | |

| Phe | Tyr | Trp | Asn | Gly | Gly | Glu | Gly | Ala | Val | Thr | Gly | Val | Asn | Lys | Ile |
|---|---|---|---|---|---|---|---|---|---|---|---|---|---|---|---|
| 225 | | | | | 230 | | | | | 235 | | | | | 240 |

| Glu | Leu | Pro | Gln | Phe | Ser | Ile | Val | Asp | Tyr | Lys | Met | Val | Ser | Lys | Lys |
|---|---|---|---|---|---|---|---|---|---|---|---|---|---|---|---|
| | | | | 245 | | | | | 250 | | | | | 255 | |

| Val | Glu | Phe | Thr | Thr | Gly | Ala | Tyr | Pro | Arg | Leu | Ser | Leu | Ser | Phe | Arg |
|---|---|---|---|---|---|---|---|---|---|---|---|---|---|---|---|
| | | | 260 | | | | | 265 | | | | | 270 | | |

| Leu | Lys | Arg | Asn | Ile | Gly | Tyr | Phe | Ile | Leu | Gln | Thr | Tyr | Met | Pro | Ser |
|---|---|---|---|---|---|---|---|---|---|---|---|---|---|---|---|
| | | 275 | | | | | 280 | | | | | 285 | | | |

| Thr | Leu | Ile | Thr | Ile | Leu | Ser | Trp | Val | Ser | Phe | Trp | Ile | Asn | Tyr | Asp |
|---|---|---|---|---|---|---|---|---|---|---|---|---|---|---|---|
| | 290 | | | | | 295 | | | | | 300 | | | | |

| Ala | Ser | Ala | Ala | Arg | Val | Ala | Leu | Gly | Ile | Thr | Thr | Val | Leu | Thr | Met |
|---|---|---|---|---|---|---|---|---|---|---|---|---|---|---|---|
| 305 | | | | | 310 | | | | | 315 | | | | | 320 |

| Thr | Thr | Ile | Ser | Thr | His | Leu | Arg | Glu | Thr | Leu | Pro | Lys | Ile | Pro | Tyr |
|---|---|---|---|---|---|---|---|---|---|---|---|---|---|---|---|
| | | | | 325 | | | | | 330 | | | | | 335 | |

| Val | Lys | Ala | Ile | Asp | Ile | Tyr | Leu | Met | Gly | Cys | Phe | Val | Phe | Val | Phe |
|---|---|---|---|---|---|---|---|---|---|---|---|---|---|---|---|
| | | | 340 | | | | | 345 | | | | | 350 | | |

| Leu | Ala | Leu | Leu | Glu | Tyr | Ala | Phe | Val | Asn | Tyr | Ile | Phe | Phe | Gly | Lys |
|---|---|---|---|---|---|---|---|---|---|---|---|---|---|---|---|
| | | 355 | | | | | 360 | | | | | 365 | | | |

| Gly | Pro | Gln | Lys | Lys | Gly | Ala | Ser | Lys | Gln | Asp | Gln | Ser | Ala | Asn | Glu |
|---|---|---|---|---|---|---|---|---|---|---|---|---|---|---|---|
| | 370 | | | | | 375 | | | | | 380 | | | | |

| Lys | Asn | Lys | Leu | Glu | Met | Asn | Lys | Val | Gln | Val | Asp | Ala | His | Gly | Asn |
|---|---|---|---|---|---|---|---|---|---|---|---|---|---|---|---|
| 385 | | | | | 390 | | | | | 395 | | | | | 400 |

| Ile | Leu | Leu | Ser | Thr | Leu | Glu | Ile | Arg | Asn | Glu | Thr | Ser | Gly | Ser | Glu |
|---|---|---|---|---|---|---|---|---|---|---|---|---|---|---|---|
| | | | | 405 | | | | | 410 | | | | | 415 | |

| Val | Leu | Thr | Gly | Val | Ser | Asp | Pro | Xaa | Xaa | Xaa | Xaa | Xaa | Xaa | Xaa | Xaa |
|---|---|---|---|---|---|---|---|---|---|---|---|---|---|---|---|
| | | | 420 | | | | | 425 | | | | | 430 | | |

| Xaa | Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|---|
| | | 435 | | | | | 440 | | | | | 445 | | | |

| Xaa | Xaa | Xaa | Xaa | Lys | Ala | Thr | Met | Tyr | Ser | Tyr | Asp | Ser | Ala | Ser | Ile | Gln |
|---|---|---|---|---|---|---|---|---|---|---|---|---|---|---|---|---|
| | 450 | | | | | 455 | | | | | 460 | | | | | |

| Tyr | Arg | Lys | Pro | Leu | Xaa | Xaa | Xaa | Xaa | Xaa | Xaa | Xaa | Xaa | Xaa | Xaa | Xaa |

```
       465                        470                      475                      480
Xaa  Xaa  Xaa  Xaa  Xaa  Xaa  Xaa  Xaa  Xaa  Xaa  Xaa  Xaa  Xaa  Xaa  Xaa  Xaa
                    485                      490                      495

Xaa  Xaa  Xaa  Xaa  Xaa  Xaa  Xaa  Xaa  Xaa  Xaa  Xaa  Xaa  Xaa  Xaa  Xaa  Xaa
                    500                      505                      510

Xaa  Ser  Ser  Arg  Glu  Gly  Phe  Gly  Arg  Gly  Leu  Asp  Xaa  Xaa  Xaa  Xaa
               515                      520                      525

Xaa  Xaa  Xaa  Xaa  Xaa  Xaa  Xaa  Xaa  Xaa  Xaa  Xaa  Xaa  Arg  His  Gly  Val
          530                      535                      540

Pro  Gly  Lys  Gly  Arg  Xaa  Xaa  Xaa  Ile  Arg  Arg  Arg  Ala  Ser  Gln
545                           550                      555                      560

Leu  Lys  Val  Lys  Ile  Pro  Asp  Leu  Thr  Asp  Val  Xaa  Xaa  Asn  Ser  Ile
                    565                      570                      575

Asp  Lys  Trp  Ser  Arg  Met  Phe  Phe  Pro  Ile  Thr  Phe  Ser  Leu  Phe  Asn
               580                      585                      590

Val  Val  Tyr  Trp  Leu  Tyr  Tyr  Val  His  Xaa  Xaa  Xaa  Xaa  Xaa  Xaa  Xaa
          595                      600                      605

Xaa  Xaa  Xaa  Xaa  Xaa  Xaa  Xaa  Xaa  Xaa
          610                      615
```

( 2 ) INFORMATION FOR SEQ ID NO:26:

( i ) SEQUENCE CHARACTERISTICS:
        ( A ) LENGTH: 617 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Met  Ser  Asp  Ser  Lys  Met  Asp  Lys  Leu  Ala  Arg  Met  Ala  Pro  Leu  Pro
1                   5                        10                       15

Arg  Thr  Pro  Leu  Leu  Thr  Ile  Trp  Leu  Ala  Ile  Asn  Met  Ala  Leu  Ile
                    20                       25                       30

Ala  Gln  Glu  Thr  Gly  His  Lys  Arg  Ile  His  Thr  Val  Gln  Ala  Ala  Thr
               35                       40                       45

Gly  Gly  Gly  Ser  Met  Leu  Gly  Asp  Val  Asn  Ile  Ser  Ala  Ile  Leu  Asp
     50                       55                       60

Ser  Phe  Ser  Val  Ser  Tyr  Asp  Lys  Arg  Val  Arg  Pro  Asn  Tyr  Gly  Gly
65                       70                       75                       80

Pro  Pro  Val  Glu  Val  Gly  Val  Thr  Met  Tyr  Val  Leu  Ser  Ile  Ser  Ser
                    85                       90                       95

Val  Ser  Glu  Val  Leu  Met  Asp  Phe  Thr  Leu  Asp  Phe  Tyr  Phe  Arg  Gln
               100                      105                      110

Phe  Trp  Thr  Asp  Pro  Arg  Leu  Ala  Tyr  Xaa  Xaa  Xaa  Xaa  Xaa  Xaa  Xaa
          115                      120                      125

Xaa  Xaa  Xaa  Arg  Lys  Arg  Pro  Gly  Val  Glu  Thr  Leu  Ser  Val  Gly  Ser
     130                      135                      140

Glu  Phe  Ile  Lys  Asn  Ile  Trp  Val  Pro  Asp  Thr  Phe  Phe  Val  Asn  Glu
145                      150                      155                      160

Lys  Gln  Ser  Tyr  Phe  His  Ile  Ala  Thr  Thr  Ser  Asn  Glu  Phe  Ile  Arg
                    165                      170                      175

Val  His  His  Ser  Gly  Ser  Ile  Thr  Arg  Ser  Ile  Arg  Leu  Thr  Ile  Thr
               180                      185                      190

Ala  Ser  Cys  Pro  Met  Asn  Leu  Gln  Tyr  Phe  Pro  Met  Asp  Arg  Gln  Leu
          195                      200                      205
```

```
Cys His Ile Glu Ile Glu Ser Phe Gly Tyr Thr Met Arg Asp Ile Arg
    210                 215                 220
Tyr Phe Trp Arg Asp Gly Leu Ser Ser Val Gly Met Ser Ser Glu Val
225             230                 235                     240
Glu Leu Pro Gln Phe Arg Val Leu Gly His Arg Gln Arg Ala Thr Glu
                245             250                 255
Ile Asn Leu Thr Thr Gly Asn Tyr Ser Arg Leu Ala Cys Glu Ile Gln
            260                 265                 270
Phe Val Arg Ser Met Gly Tyr Tyr Leu Ile Gln Ile Tyr Ile Pro Ser
        275             280                 285
Gly Leu Ile Val Val Ile Ser Trp Val Ser Phe Trp Leu Asn Arg Asn
    290             295                 300
Ala Thr Pro Ala Arg Val Ala Leu Gly Val Thr Thr Val Leu Thr Met
305             310                 315                     320
Thr Thr Leu Met Ser Ser Thr Asn Ala Ala Leu Pro Lys Ile Ser Tyr
                325             330                 335
Val Lys Ser Ile Asp Val Tyr Leu Gly Thr Cys Phe Val Met Val Phe
            340                 345                 350
Ala Ser Leu Leu Glu Tyr Ala Thr Val Gly Tyr Met Ala Lys Arg Ile
        355             360                 365
Gln Met Arg Lys Gln Arg Phe Met Ala Ile Gln Lys Ile Ala Glu Gln
    370             375                 380
Lys Lys Gln Gln Leu Asp Gly Ala Asn Gln Gln Gln Ala Asn Pro Asn
385             390                 395                     400
Pro Asn Ala Asn Val Gly Gly Pro Gly Gly Val Gly Val Gly Pro Gly
                405             410                 415
Gly Pro Gly Gly Pro Gly Gly Gly Val Asn Val Gly Val Gly Met Gly
        420             425                 430
Met Gly Pro Glu His Gly His Gly His Gly His His Ala His Ser His
    435             440                 445
Gly His Pro His Ala Pro Lys Gln Thr Val Ser Asn Arg Pro Ile Gly
450             455                 460
Phe Ser Asn Ile Gln Gln Asn Val Gly Thr Arg Gly Cys Ser Ile Val
465             470                 475                     480
Gly Pro Leu Phe Gln Glu Val Arg Phe Lys Val His Asp Pro Lys Ala
                485             490                 495
His Ser Lys Gly Gly Thr Leu Glu Asn Thr Val Asn Gly Gly Arg Gly
            500                 505                 510
Gly Pro Gln Ser His Gly Pro Gly Pro Gly Gln Gly Gly Gly Pro Pro
        515             520                 525
Gly Gly Gly Gly Gly Gly Gly Gly Gly Gly Pro Pro Glu Gly Gly
    530             535                 540
Gly Asp Pro Glu Ala Ala Val Pro Ala His Leu Leu His Pro Gly Lys
545             550                 555                     560
Val Lys Lys Asp Ile Asn Lys Leu Leu Gly Ile Thr Pro Ser Asp Ile
                565             570                 575
Asp Lys Tyr Ser Arg Ile Val Phe Pro Val Cys Phe Val Cys Phe Asn
            580                 585                 590
Leu Met Tyr Trp Ile Ile Tyr Leu His Val Ser Asp Val Val Ala Asp
        595             600                 605
Asp Leu Val Leu Leu Gly Glu Glu Xaa
    610             615
```

( 2 ) INFORMATION FOR SEQ ID NO:27:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:27:

Arg Arg Xaa Ser Xaa
1               5

( 2 ) INFORMATION FOR SEQ ID NO:28:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:28:

Cys Phe Val Phe Val Phe
1               5

( 2 ) INFORMATION FOR SEQ ID NO:29:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:29:

Val Phe Val Phe Ala Ala Leu
1               5

( 2 ) INFORMATION FOR SEQ ID NO:30:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:30:

Ala Ala Thr Ala Ala Ala
1               5

( 2 ) INFORMATION FOR SEQ ID NO:31:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:31:

Ala Thr Val Asn Tyr Phe Thr
1               5